United States Patent
Han et al.

(10) Patent No.: US 12,410,151 B2
(45) Date of Patent: Sep. 9, 2025

(54) FLUORENE DERIVATIVE AND ORGANIC LIGHT EMITTING DEVICE COMPRISING SAME

(71) Applicant: LG CHEM, LTD., Seoul (KR)

(72) Inventors: Miyeon Han, Daejeon (KR); Dong Hoon Lee, Daejeon (KR); Jungoh Huh, Daejeon (KR); Boonjae Jang, Daejeon (KR); Dong Uk Heo, Daejeon (KR); Junghoon Yang, Daejeon (KR); Heekyung Yun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 18/612,944

(22) Filed: Mar. 21, 2024

(65) Prior Publication Data

US 2024/0292745 A1 Aug. 29, 2024

Related U.S. Application Data

(63) Continuation of application No. 16/629,304, filed as application No. PCT/KR2018/008406 on Jul. 25, 2018, now Pat. No. 12,010,911.

(30) Foreign Application Priority Data

Jul. 28, 2017 (KR) .................. 10-2017-0096148

(51) Int. Cl.
*C07D 401/10* (2006.01)
*C07D 251/24* (2006.01)
(Continued)

(52) U.S. Cl.
CPC ......... *C07D 401/10* (2013.01); *C07D 251/24* (2013.01); *H10K 85/30* (2023.02);
(Continued)

(58) Field of Classification Search
CPC .. C07D 251/24; C07D 401/10; C07D 403/10; H01L 51/0052; H01L 51/0067;
(Continued)

(56) References Cited

U.S. PATENT DOCUMENTS

| 2007/0051944 A1 | 3/2007 | Vestweber ........... C07D 239/26 257/E51.012 |
| 2011/0121274 A1 | 5/2011 | Parham .............. H01L 51/0058 252/301.16 |

(Continued)

FOREIGN PATENT DOCUMENTS

| CN | 102421868 | 4/2012 |
| CN | 109071465 | 12/2018 |

(Continued)

OTHER PUBLICATIONS

WO-2017171376-A1 machine translation (Year: 2017).*

*Primary Examiner* — Elizabeth M. Dahlburg
(74) *Attorney, Agent, or Firm* — Bryan Cave Leighton Paisner LLP

(57) ABSTRACT

A fluorene derivative of any of Chemical Formula 1-1 to Chemical Formula 1-3:

[Chemical Formula 1-1]

(Continued)

-continued

[Chemical Formula 1-2]

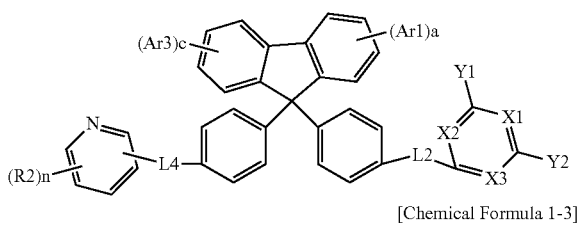

[Chemical Formula 1-3]

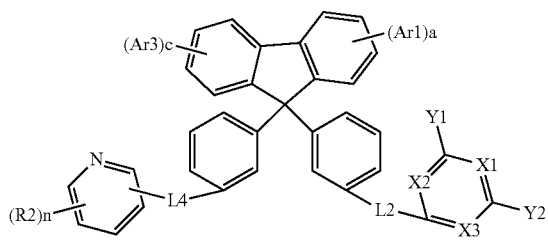

wherein: Ar1 and Ar3 are hydrogen; L2 and L4 each independently is a direct bond, or a substituted or unsubstituted arylene or heteroarylene group; a and c are 4; X1 to X3 are each independently N or CR1 providing two or more of X1 to X3 are N; R1, R2, Y1 and Y2 are each independently hydrogen, deuterium, a substituted or unsubstituted alkyl group, a substituted or unsubstituted silyl group, a substituted or unsubstituted alkoxy group, a substituted or unsubstituted aryl group, or a substituted or unsubstituted heteroaryl group; and n is an integer of 0 to 4, and when n is 2 to 4, the R2s are the same as or different from each other; and an organic light emitting device including the same.

8 Claims, 1 Drawing Sheet

(51) Int. Cl.
*H10K 85/30* (2023.01)
*H10K 85/60* (2023.01)
*H10K 50/11* (2023.01)
*H10K 50/15* (2023.01)
*H10K 50/16* (2023.01)
*H10K 50/17* (2023.01)

(52) U.S. Cl.
CPC ........... *H10K 85/654* (2023.02); *H10K 50/11* (2023.02); *H10K 50/15* (2023.02); *H10K 50/16* (2023.02); *H10K 50/17* (2023.02); *H10K 50/171* (2023.02)

(58) Field of Classification Search
CPC ............ H01L 51/0077; H01L 51/5012; H01L 51/5016; H01L 51/5056; H01L 51/506; H01L 51/5064; H01L 51/5072; H01L 51/5076; H01L 51/508; H01L 51/5088; H01L 51/5092; H01L 51/5096; H10K 50/11; H10K 50/15; H10K 50/155; H10K 50/156; H10K 50/16; H10K 50/165; H10K 50/166; H10K 50/17; H10K 50/171; H10K 50/18; H10K 85/30; H10K 85/615; H10K 85/654; H10K 2101/10
See application file for complete search history.

(56) References Cited

U.S. PATENT DOCUMENTS

| | | |
|---|---|---|
| 2012/0056171 A1 | 3/2012 | Kim et al. |
| 2012/0228554 A1 | 9/2012 | Franz ................... C07D 403/14 252/301.16 |
| 2015/0162543 A1 | 6/2015 | Lee ....................... C07D 405/14 136/263 |
| 2018/0222872 A1 | 8/2018 | Jatsch ................. H01L 51/5016 |

FOREIGN PATENT DOCUMENTS

| | | | |
|---|---|---|---|
| JP | 2009182088 | 8/2009 | |
| KR | 10-20120031684 | 4/2012 | |
| KR | 10-20120092908 | 8/2012 | |
| KR | 10-20140009019 | 1/2014 | |
| KR | 10-20170113342 | 10/2017 | |
| KR | 10-1850243 | 4/2018 | |
| WO | WO-2017171376 A1 | 10/2017 | ........... C07C 13/567 |

\* cited by examiner

[FIG. 1]
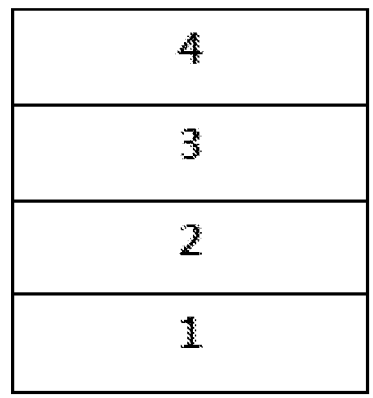
[FIG. 2]
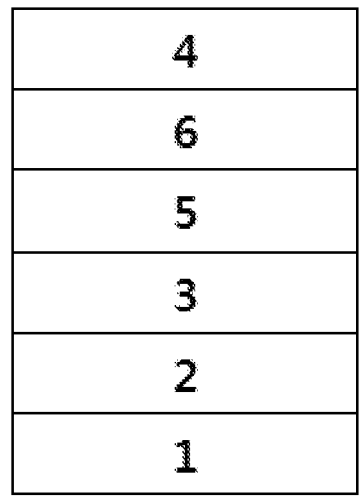

FLUORENE DERIVATIVE AND ORGANIC LIGHT EMITTING DEVICE COMPRISING SAME

CROSS-REFERENCE TO RELATED APPLICATIONS

This application is continuation of U.S. patent application Ser. No. 16/629,304, filed on Jan. 7, 2020, which is a National Stage Application of International Application No. PCT/KR2018/008406 filed on Jul. 25, 2018, which claims priority to and the benefits of Korean Patent Application No. 10-2017-0096148, filed with the Korean Intellectual Property Office on Jul. 28, 2017, the entire contents of which are incorporated herein by reference.

TECHNICAL FIELD

The present specification relates to a fluorene derivative and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

Technical Problem

The present specification is directed to providing a fluorene derivative and an organic light emitting device including the same.

Technical Solution

One embodiment of the present specification provides a fluorene core structure of Chemical Formula 1:

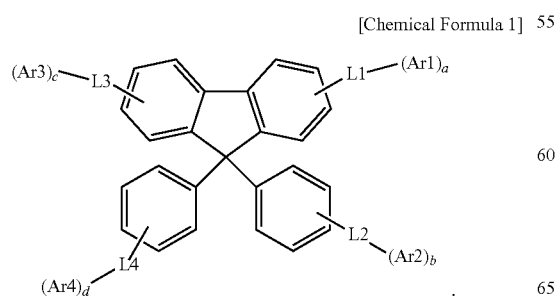

[Chemical Formula 1]

In Chemical Formula 1:

Ar1 and Ar2 are the same as or different from each other, and each independently is hydrogen or the following Chemical Formula 2, and at least one of Ar1 and Ar2 is Chemical Formula 2;

Ar3 and Ar4 are the same as or different from each other, and each independently is hydrogen or the following Chemical Formula 3, and at least one of Ar3 and Ar4 is Chemical Formula 3;

L1 to L4 are the same as or different from each other, and each independently is a direct bond, a substituted or unsubstituted arylene group, or a substituted or unsubstituted heteroarylene group;

Ar1 and Ar3 bond to a symmetric position of a core structure;

Ar2 and Ar4 bond to a symmetric position of a core structure;

a and c are an integer of 0 to 4;

b and d are an integer of 0 to 5;

when a is a plural number, the Ar1s are the same as or different from each other;

when b is a plural number, the Ar2s are the same as or different from each other;

when c is a plural number, the Ar3s are the same as or different from each other; and when d is a plural number, the Ar4s are the same as or different from each other,

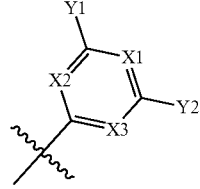

[Chemical Formula 2]

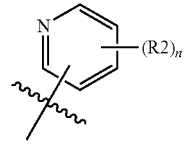

[Chemical Formula 3]

wherein in Chemical Formulae 2 and 3:

is a site bonding to Chemical Formula 1;

X1 to X3 are the same as or different from each other, and each independently is N or CR1;

two or more of X1 to X3 are N;

R1, R2, Y1 and Y2 are the same as or different from each other, and each independently is hydrogen, deuterium, a substituted or unsubstituted alkyl group, a substituted or unsubstituted silyl group, a substituted or unsubstituted alkoxy group, a substituted or unsubstituted aryl group, or a substituted or unsubstituted heteroaryl group; and n is an integer of 0 to 4, and when n is a plural number, the R2s are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the fluorene derivative of Chemical Formula 1.

Advantageous Effects

A fluorene derivative according to one embodiment of the present specification can be used as a material of an organic material layer of an organic light emitting device, and by using the same, efficiency can be enhanced, a low driving voltage can be obtained and/or lifetime properties can be enhanced in the organic light emitting device.

DESCRIPTION OF DRAWINGS

FIG. 1 illustrates an organic light emitting device according to one embodiment of the present specification.
FIG. 2 illustrates an organic light emitting device according to one embodiment of the present specification.

REFERENCE NUMERALS

1: Substrate
2: First Electrode
3: Organic Material Layer
4: Second Electrode
5: Light Emitting Layer
6: Electron Injection and Transfer Layer

MODE FOR DISCLOSURE

Herein, the present specification will be described in more detail.

One embodiment of the present specification provides a fluorene derivative of Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

The term "substituted or unsubstituted" in the present specification means being substituted with one, two or more substituents selected from the group consisting of deuterium, a nitrile group, a substituted or unsubstituted alkyl group, a substituted or unsubstituted cycloalkyl group, a substituted or unsubstituted silyl group, a substituted or unsubstituted aryl group, and a substituted or unsubstituted heterocyclic group, or being substituted with a substituent linking two or more substituents among the substituents illustrated above, or having no substituents. For example, "a substituent linking two or more substituents" can include an aryl group substituted with an aryl group, an aryl group substituted with a heteroaryl group, a heterocyclic group substituted with an aryl group, an aryl group substituted with an alkyl group, and the like.

In the present specification, the alkyl group can be linear or branched, and although not particularly limited thereto, the number of carbon atoms is preferably from 1 to 30. Specific examples thereof can include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 30 carbon atoms. Specific examples thereof can include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tertbutyl-cyclohexyl, cycloheptyl, cyclooctyl and the like, but are not limited thereto.

In the present specification, specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

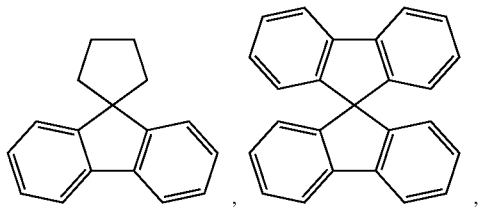

,

-continued

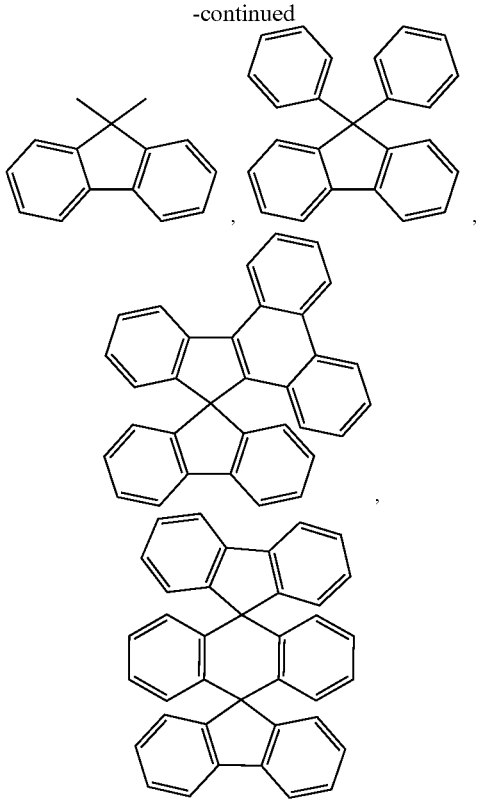

and the like can be included. However, the compound is not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups. For example, the aryl group in the arylamine group can be selected from among the examples of the aryl group described above.

In the present specification, the aryl group in the aryloxy group, the N-arylalkylamine group and the N-arylheteroarylamine group is the same as the examples of the aryl group described above. Specific examples of the aryloxy group can include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heteroaryl group can be monocyclic or polycyclic. Examples of the heterocyclic group can include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group has the same definition as the aryl group except for being divalent.

In the present specification, the heteroarylene group has the same definition as the heteroaryl group except for being divalent.

According to one embodiment of the present specification, in Chemical Formula 3, the R2 group can substitute at a position number 2 when a site bonding to L3 or L4 is number 1.

According to one embodiment of the present specification, in Chemical Formula 3, the R2 group can substitute at a position number 3 when a site bonding to L3 or L4 is number 1.

According to one embodiment of the present specification, in Chemical Formula 3, the R2 group can substitute at a position number 4 when a site bonding to L3 or L4 is number 1.

According to one embodiment of the present specification, the fluorene derivative of Chemical Formula 1 can be a compound of any one of the following Chemical Formulae A and B:

[Chemical Formula A]

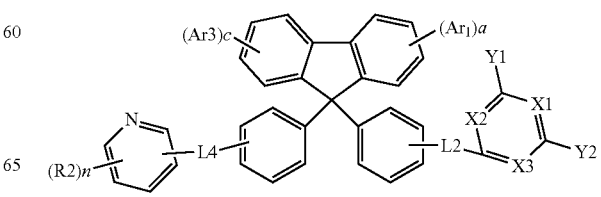

[Chemical Formula B]

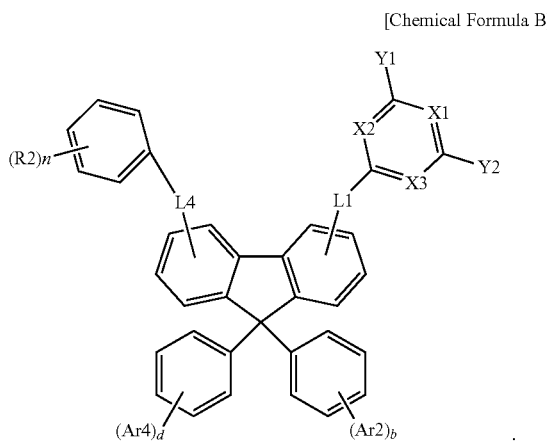

In Chemical Formulae A and B, Ar1 to Ar4, R2, a to d, X1 to X3, Y1, Y2, L1 to L4, and n have the same definitions as in Chemical Formula 1.

According to one embodiment of the present specification, the fluorene derivative of Chemical Formula 1 can be a compound of any one of the following Chemical Formulae 1-1 to 1-6:

[Chemical Formula 1-1]

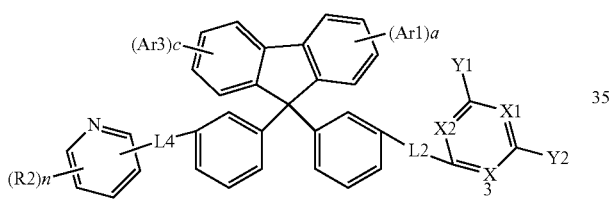

[Chemical Formula 1-2]

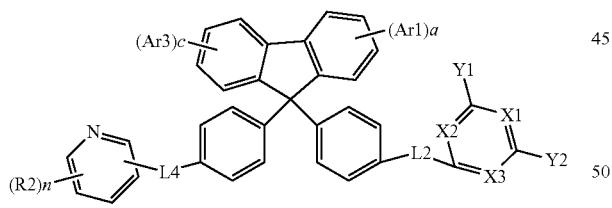

[Chemical Formula 1-3]

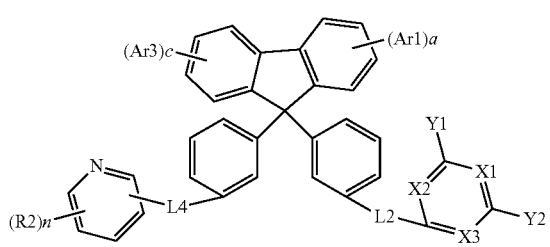

[Chemical Formula 1-4]

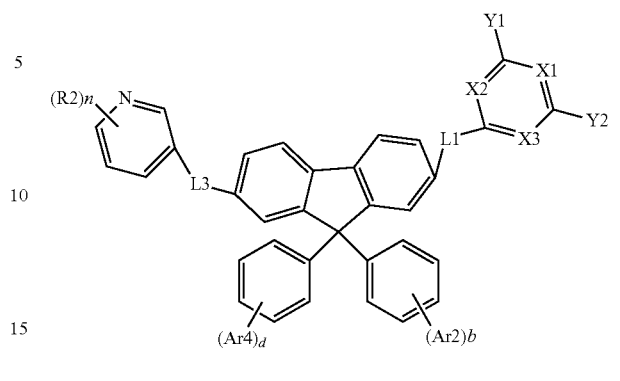

[Chemical Formula 1-5]

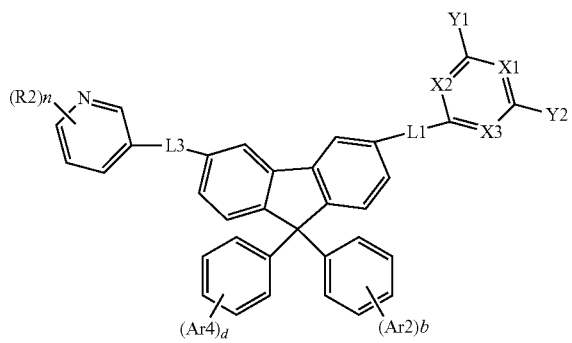

[Chemical Formula 1-6]

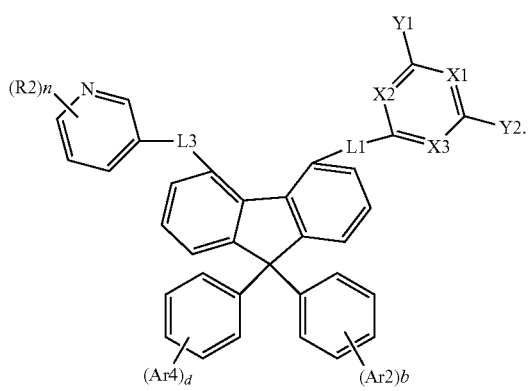

In Chemical Formulae 1-1 to 1-6, Ar1 to Ar4, R1, R2, a to d, X1 to X3, Y1, Y2, L1 to L4, and n have the same definitions as in Chemical Formula 1.

In the present specification, the "symmetric position" refers to a position forming a reflection symmetry around the following dotted line passing through a position number 9 of the fluorene core structure. For example, in the following structural formula, two *1s are in a symmetric position, and likewise, two *2s to *9s are each in a symmetric position.

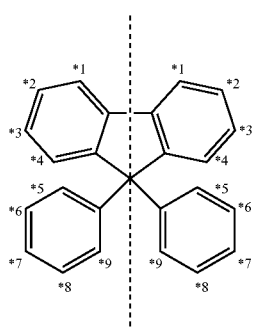

In the present specification, the "core structure" means

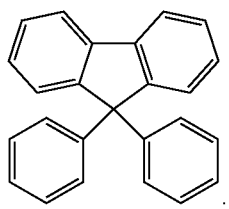 [SMILES: c1ccc(C2(c3ccccc3)c3ccccc3-c3ccccc32)cc1]

According to one embodiment of the present specification, X1 to X3 are the same as or different from each other, and each independently is N or CR1.

According to one embodiment of the present specification, at least two or more of X1 to X3 are N.

According to one embodiment of the present specification, R1, R2, Y1 and Y2 are the same as or different from each other, and each independently is hydrogen, deuterium, a substituted or unsubstituted alkyl group, a substituted or unsubstituted silyl group, a substituted or unsubstituted alkoxy group, a substituted or unsubstituted aryl group, or a substituted or unsubstituted heteroaryl group.

According to one embodiment of the present specification, R1 and R2 are hydrogen.

According to one embodiment of the present specification, Y1 and Y2 are the same as or different from each other, and each independently is hydrogen, deuterium, or a substituted or unsubstituted aryl group.

According to one embodiment of the present specification, Y1 and Y2 are the same as or different from each other, and each independently is a substituted or unsubstituted aryl group having 6 to 20 carbon atoms.

According to one embodiment of the present specification, Y1 and Y2 are the same as or different from each other, and each independently is an aryl group having 6 to 20 carbon atoms unsubstituted or substituted with an alkyl group.

According to one embodiment of the present specification, Y1 and Y2 are the same as or different from each other, and each independently is a phenyl group unsubstituted or substituted with an alkyl group having 1 to 10 carbon atoms, or a biphenyl group.

According to one embodiment of the present specification, Y1 and Y2 are the same as or different from each other, and each independently is a phenyl group unsubstituted or substituted with a methyl group, or a biphenyl group.

According to one embodiment of the present specification, L1 to L4 are the same as or different from each other, and each independently is a direct bond, a substituted or unsubstituted arylene group, or a substituted or unsubstituted heteroarylene group.

According to one embodiment of the present specification, L1 to L4 are the same as or different from each other, and each independently is a direct bond, a substituted or unsubstituted arylene group having 6 to 20 carbon atoms, or a substituted or unsubstituted monocyclic or polycyclic heteroarylene group having 3 to 20 carbon atoms.

According to one embodiment of the present specification, L1 and L2 are the same as or different from each other, and each independently is a direct bond or a phenylene group.

According to one embodiment of the present specification, L3 and L4 are the same as or different from each other, and each independently is a direct bond, a substituted or unsubstituted phenylene group, a substituted or unsubstituted biphenylylene group, a substituted or unsubstituted naphthylene group, a substituted or unsubstituted phenanthrene group, a divalent fluorene group unsubstituted or substituted with an alkyl group, or a divalent fluorene group unsubstituted or substituted with an aryl group.

According to one embodiment of the present specification, L3 and L4 are the same as or different from each other, and each independently is a direct bond, a phenylene group, a biphenylylene group, a naphthylene group, a phenanthrene group, or a divalent fluorene group unsubstituted or substituted with an alkyl group having 1 to 10 carbon atoms.

According to one embodiment of the present specification, L3 and L4 are the same as or different from each other, and each independently is a direct bond, a phenylene group, a biphenylylene group, a naphthylene group, a phenanthrene group, or a divalent dimethylfluorene group.

According to one embodiment of the present specification, L1 to L4 are the same as or different from each other, and each independently is any one of the following substituents:

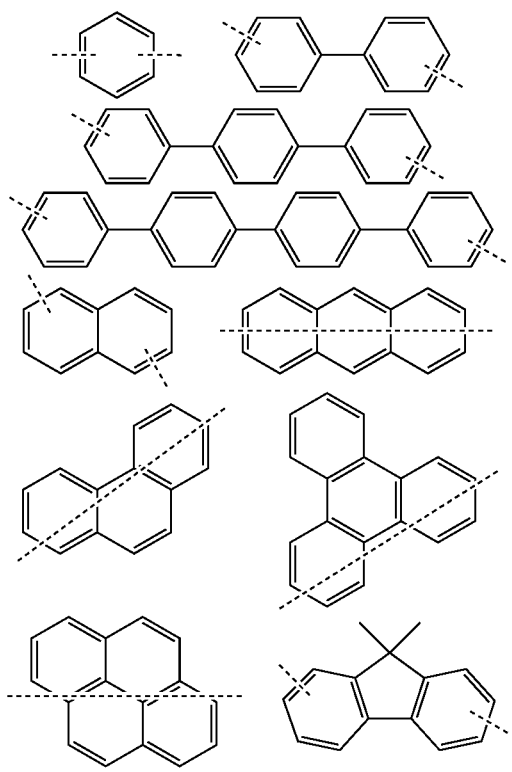

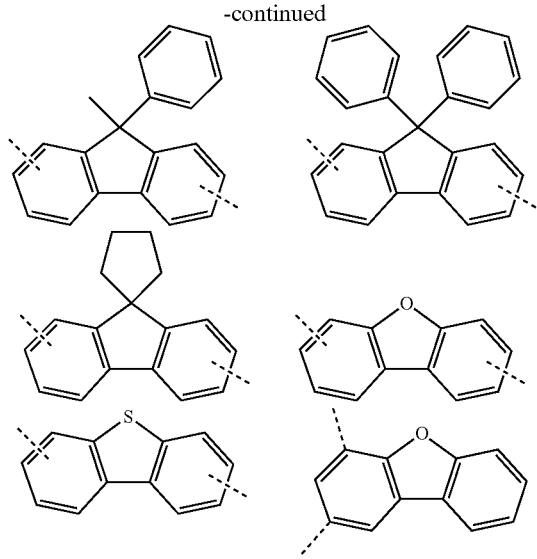
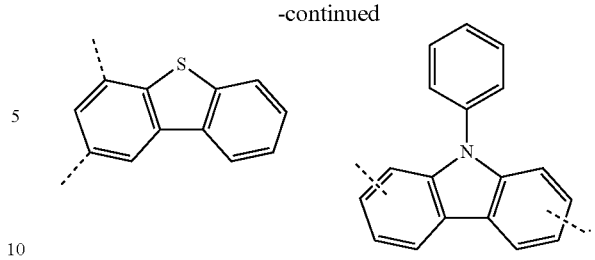

According to one embodiment of the present specification, Chemical Formula 2 is a triazine group unsubstituted or substituted with an aryl group having 6 to 20 carbon atoms, or a pyrimidine group unsubstituted or substituted with an aryl group having 6 to 20 carbon atoms.

According to another embodiment of the present specification, the fluorene derivative of Chemical Formula 1 can be selected from among the following compounds:

cpd 1

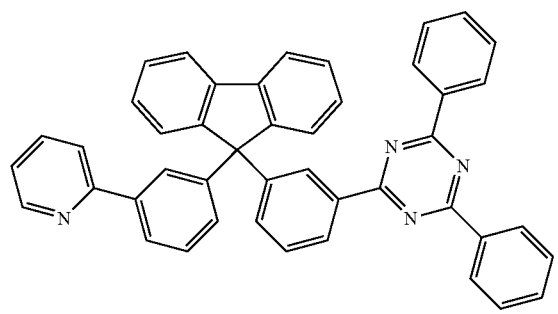

cpd 2

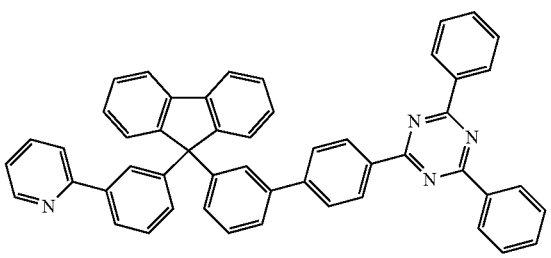

cpd 3

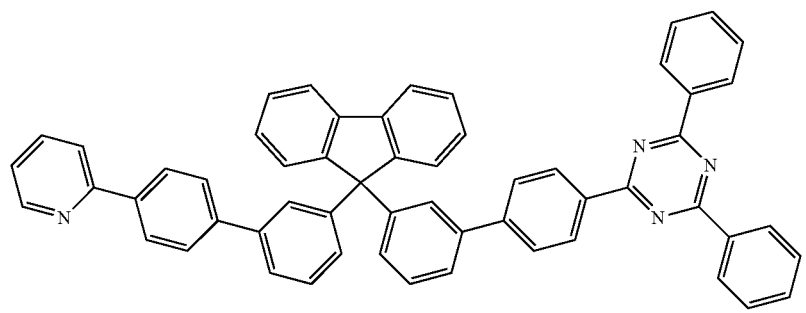

cpd 4

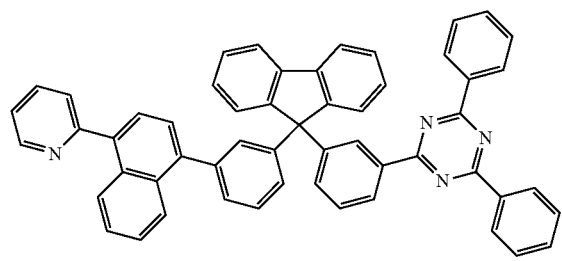

cpd 5

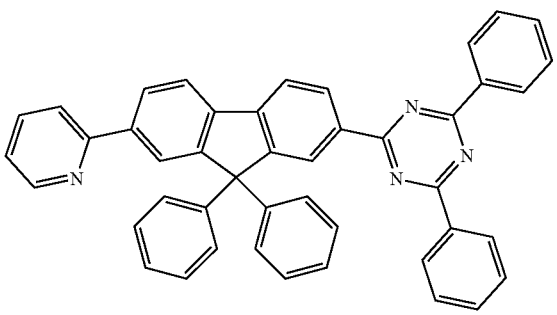

-continued
cpd 6
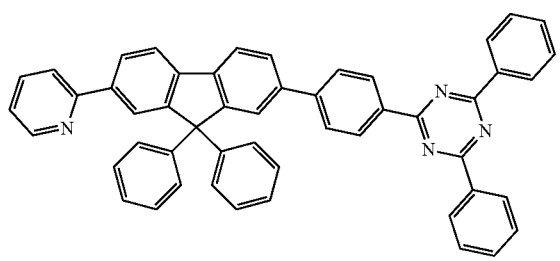
cpd 7
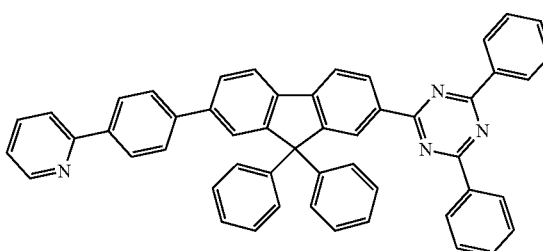
cpd 8
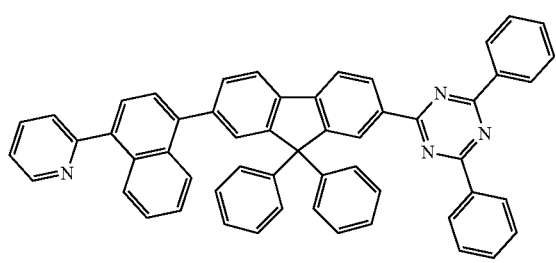
cpd 9
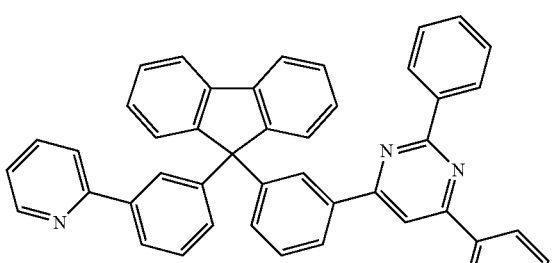
cpd 10
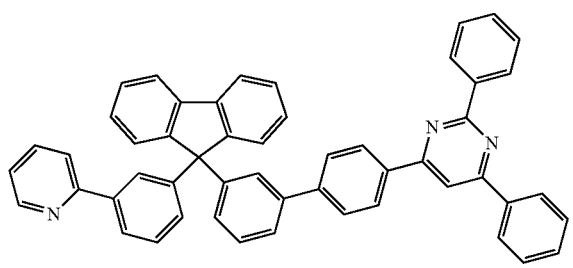
cpd 11
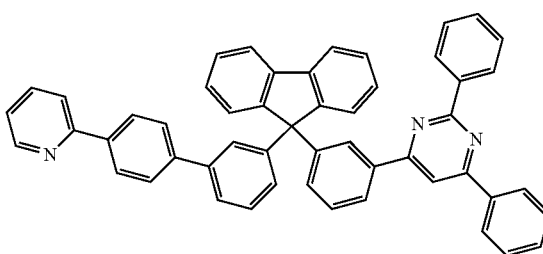
cpd 12
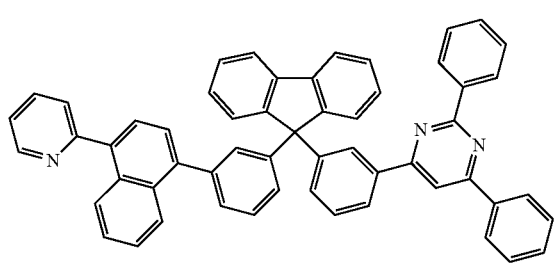
cpd 13
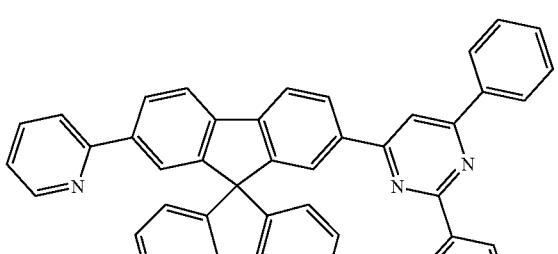
cpd 14
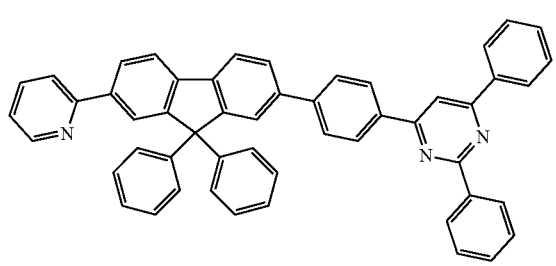
cpd 15
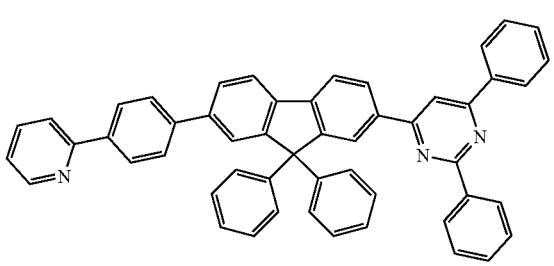

-continued
cpd 15
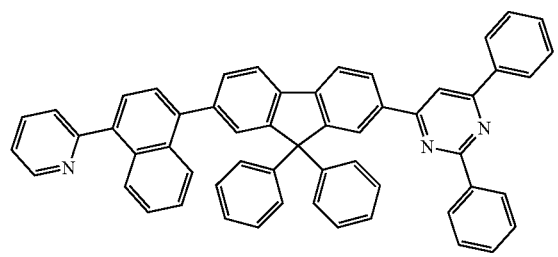
cpd 16
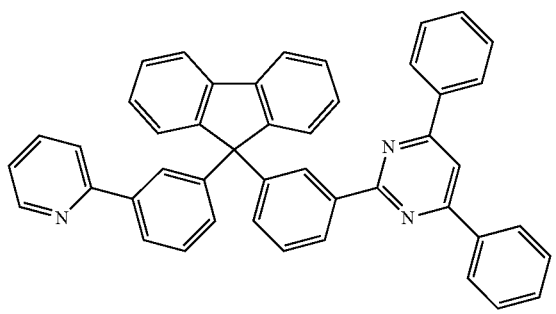
cpd 17
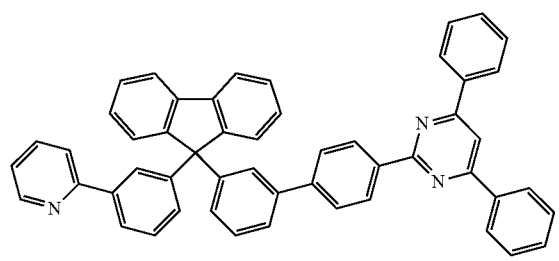
cpd 18
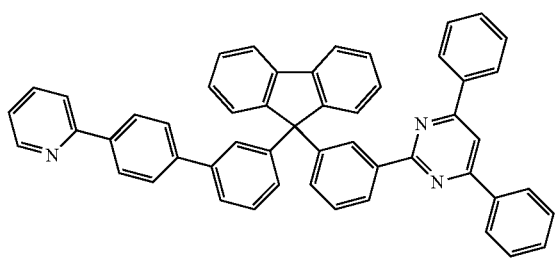
cpd 20
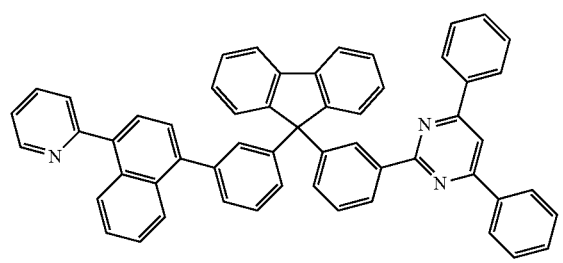
cpd 21
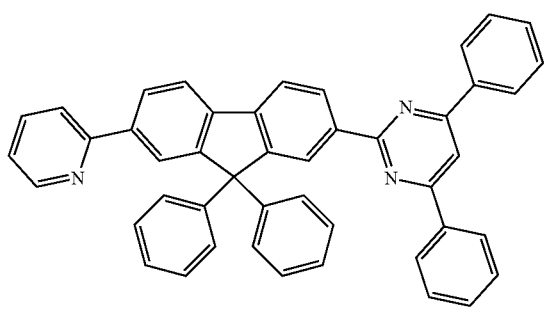
cpd 22
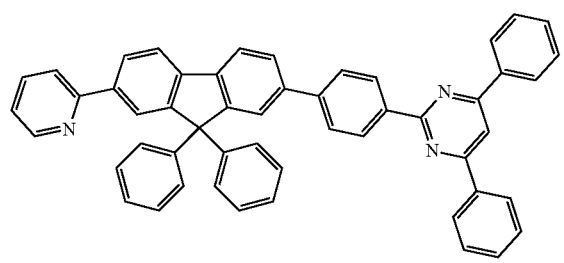
cpd 23
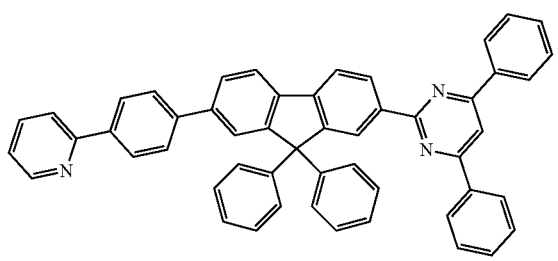
cpd 24
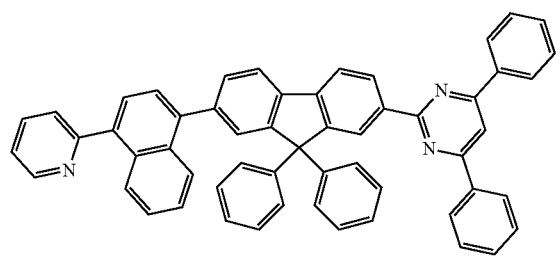
cpd 25
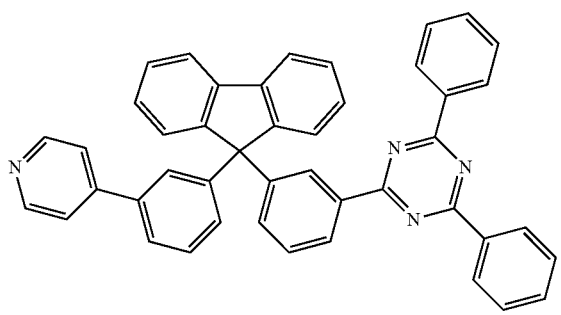

-continued
cpd 26
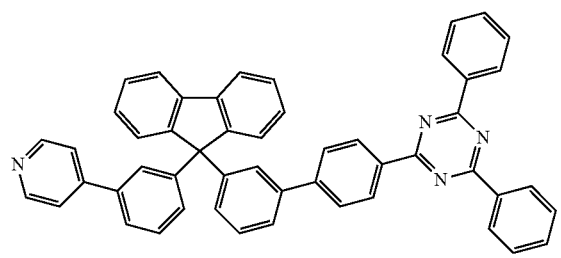
cpd 27
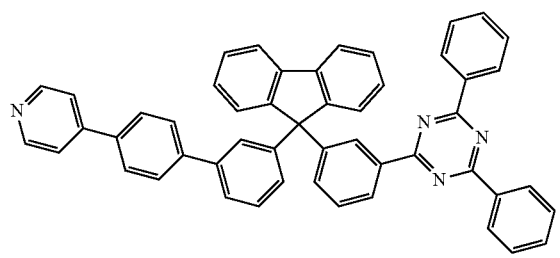
cpd 28
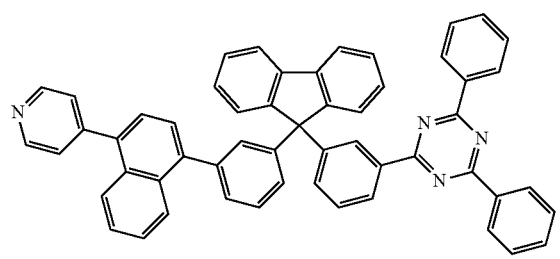
cpd 29
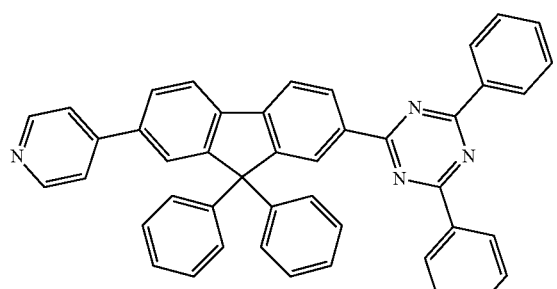
cpd 30
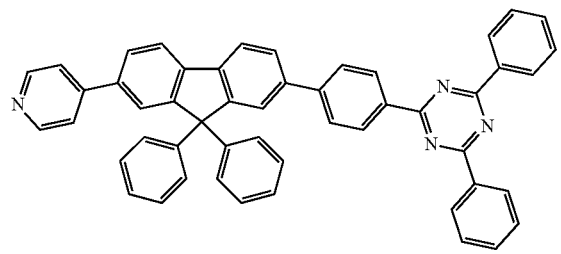
cpd 31
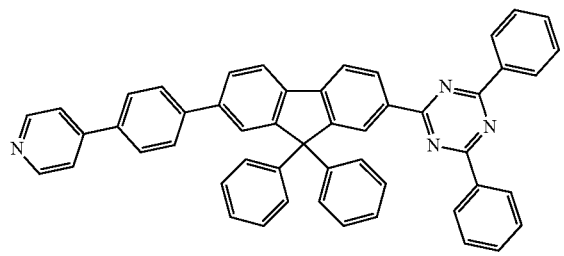
cpd 32
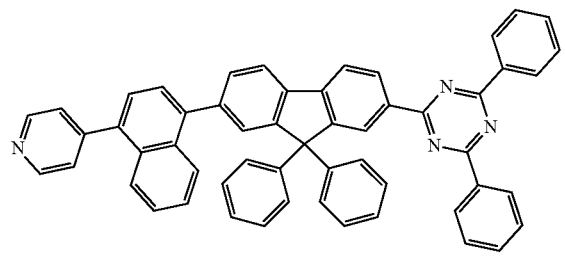
cpd 33
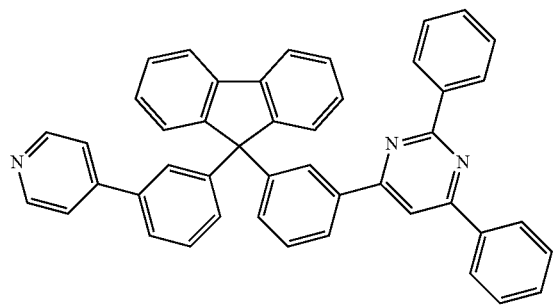
cpd 34
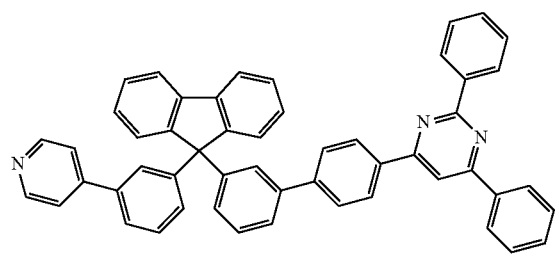

-continued
cpd 36
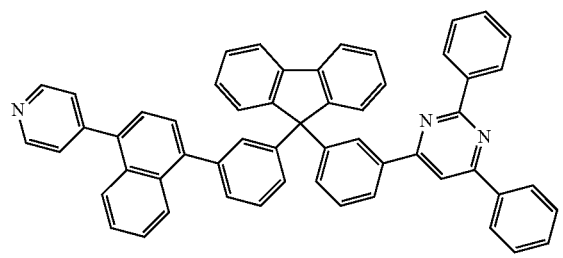
cpd 37
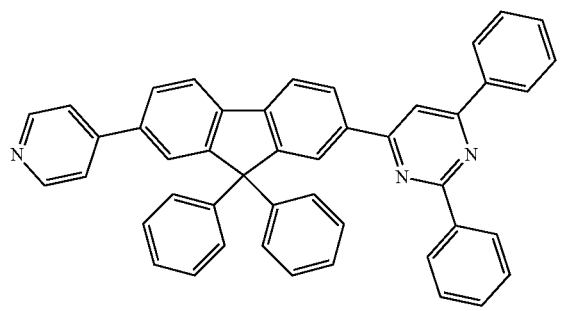
cpd 38
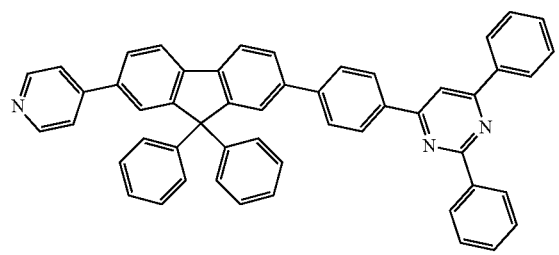
cpd 39
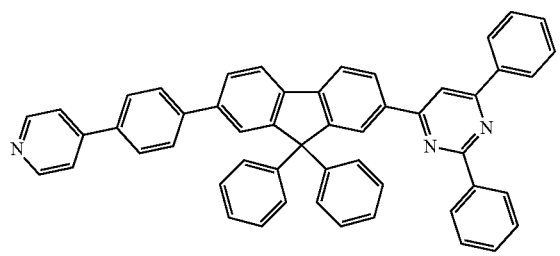
cpd 40
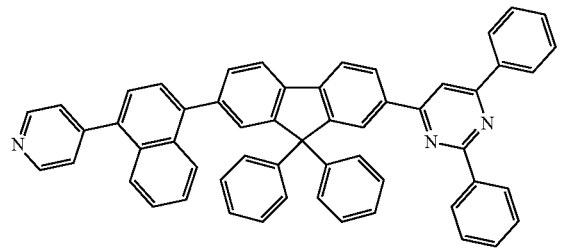
cpd 41
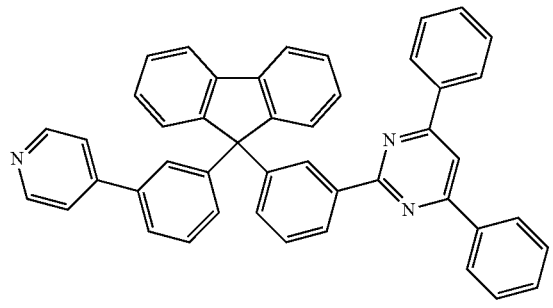
cpd 42
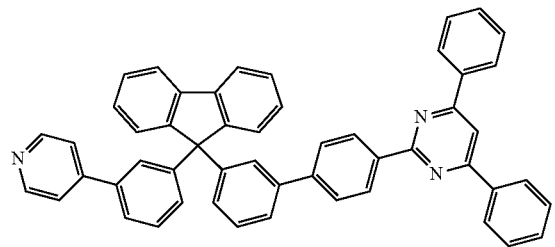
cpd 43
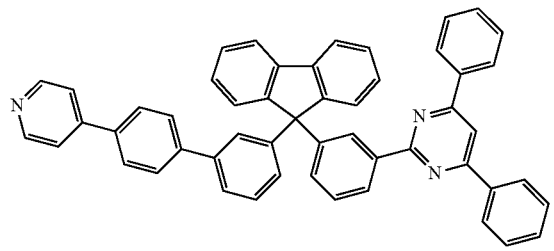
cpd 44
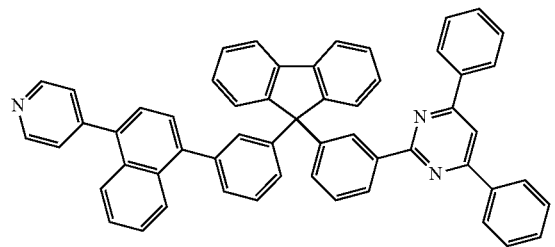
cpd 45
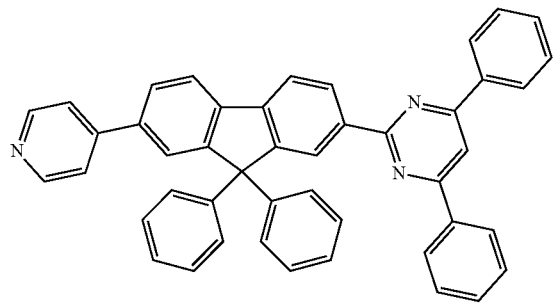

-continued
cpd 46
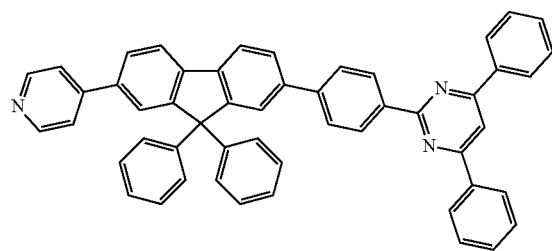
cpd 47
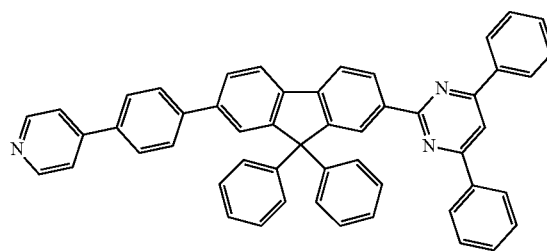
cpd 48
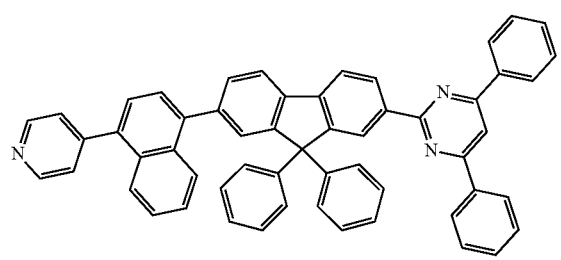
cpd 49
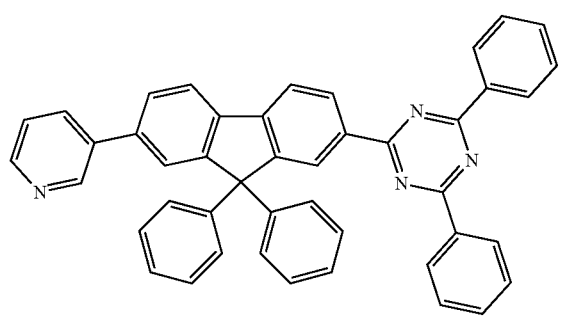
cpd 50
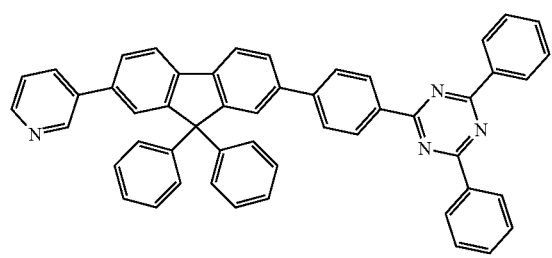
cpd 51
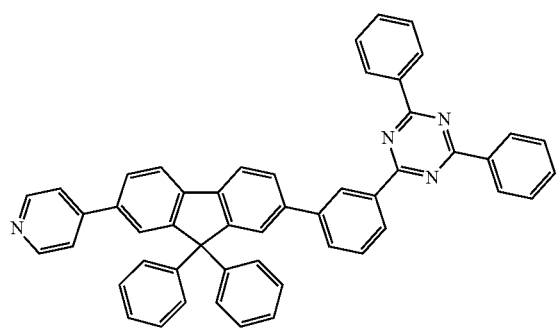
cpd 52
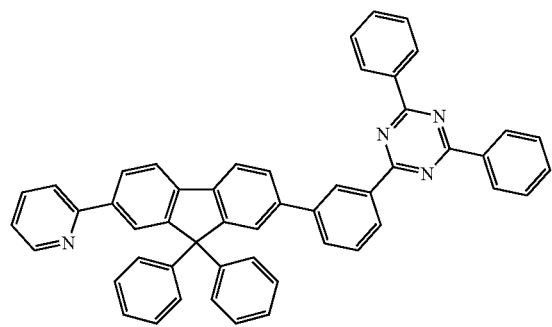
cpd 53
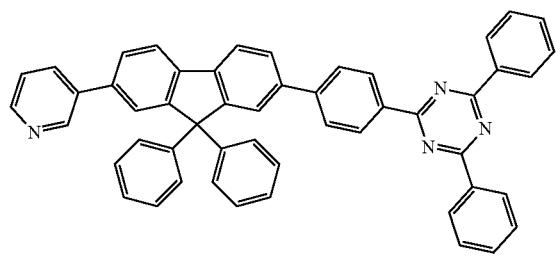

-continued
cpd 54
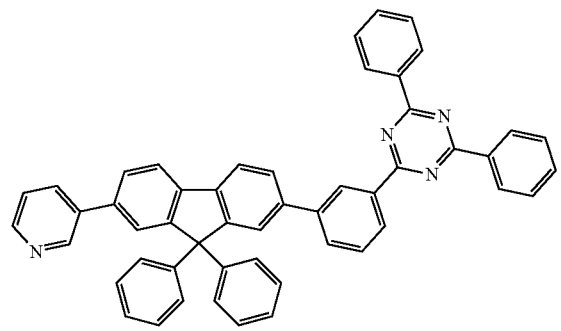
cpd 55
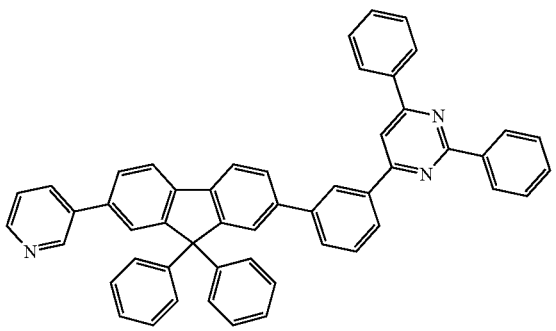
cpd 56
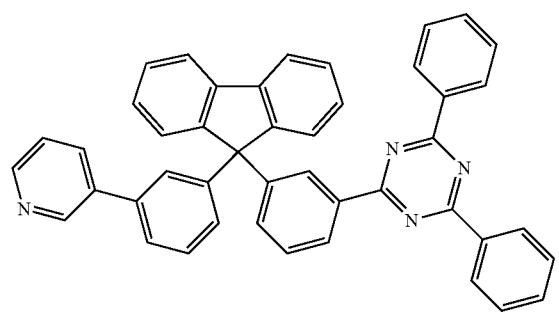
cpd 57
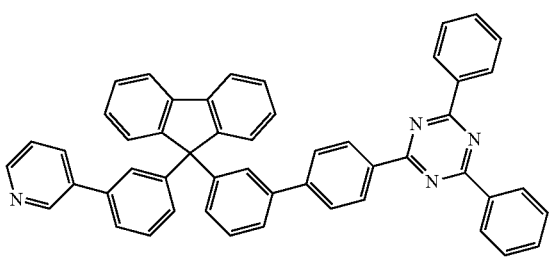
cpd 58
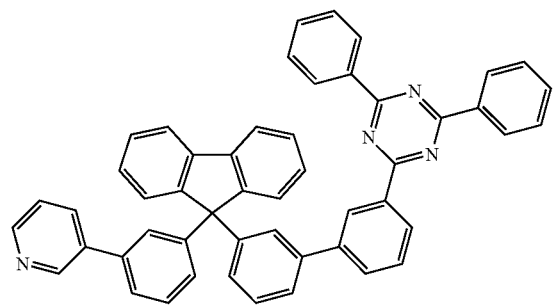
cpd 59
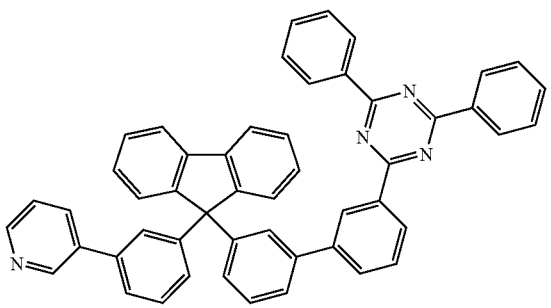
cpd 60
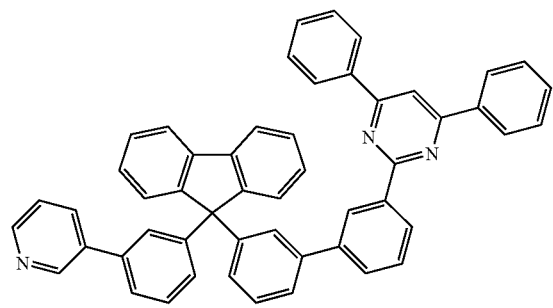
cpd 61
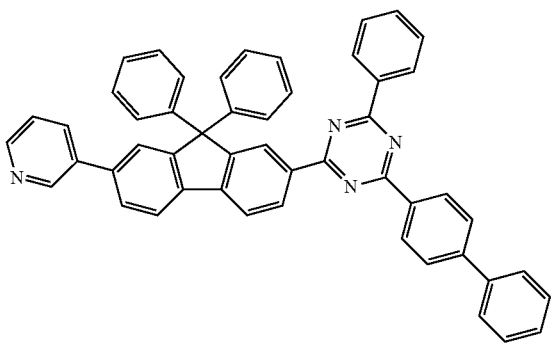

-continued
cpd 62
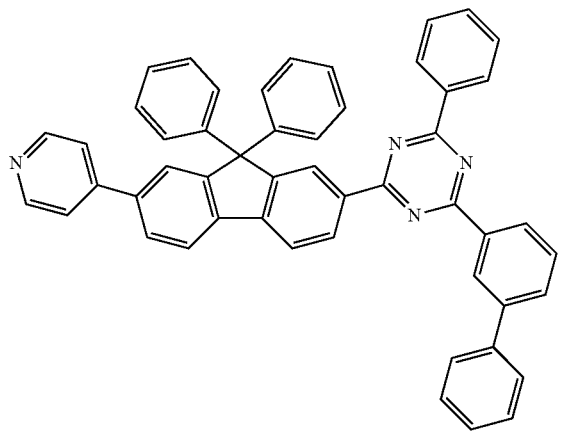
cpd 63
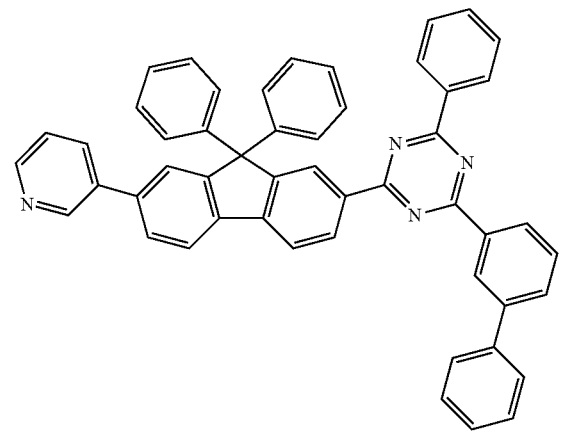
cpd 64
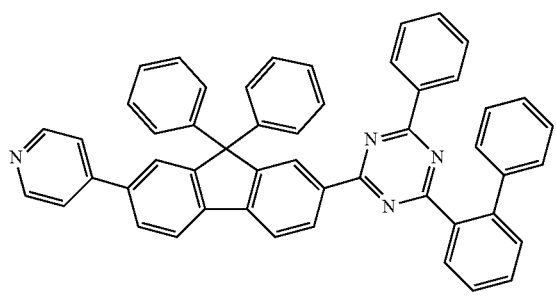
cpd 65
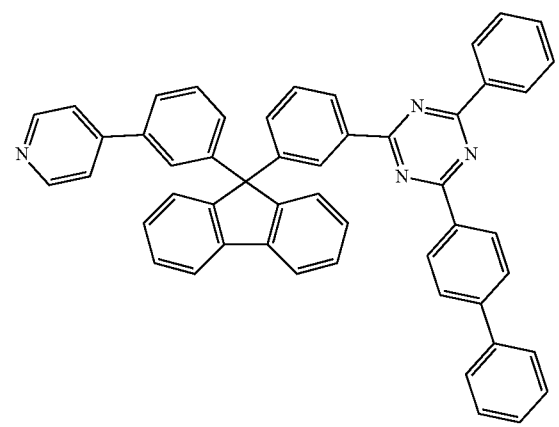
cpd 66
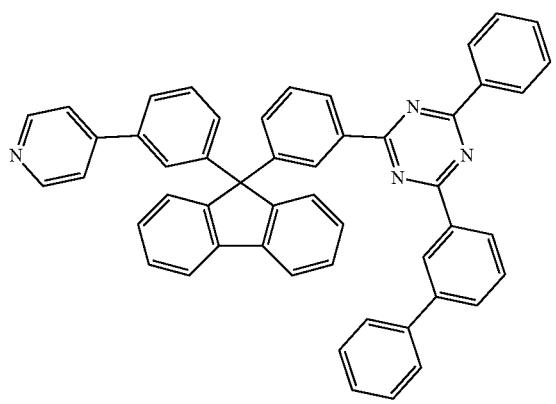
cpd 67
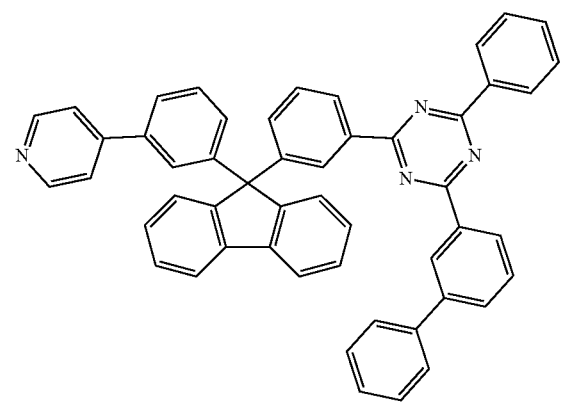

-continued
cpd 68
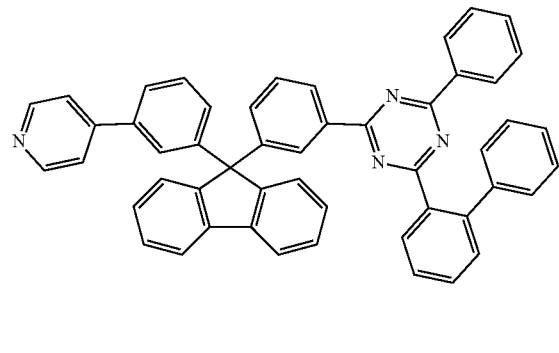
cpd 69
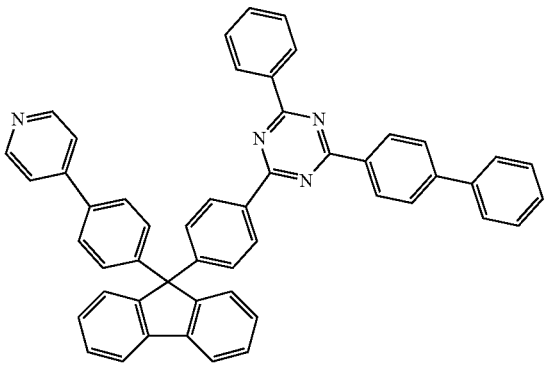
cpd 70
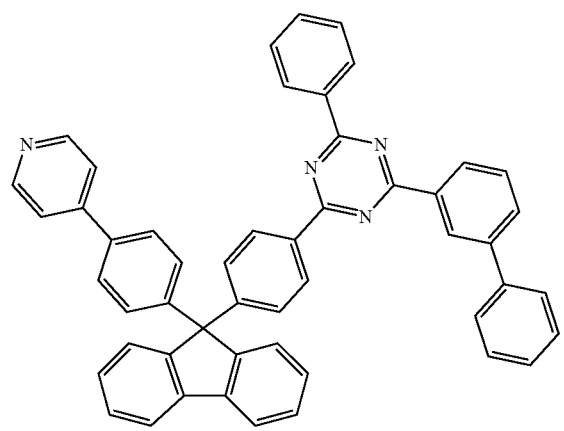
cpd 71
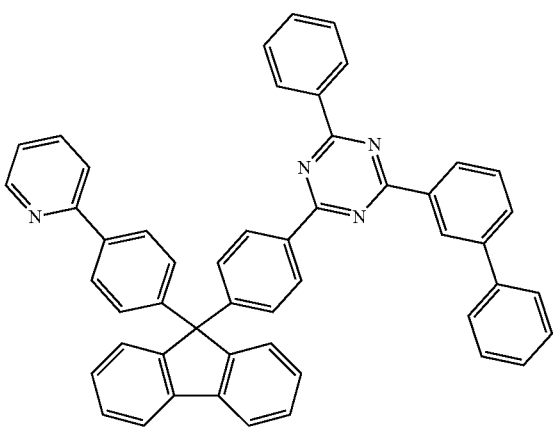
cpd 72
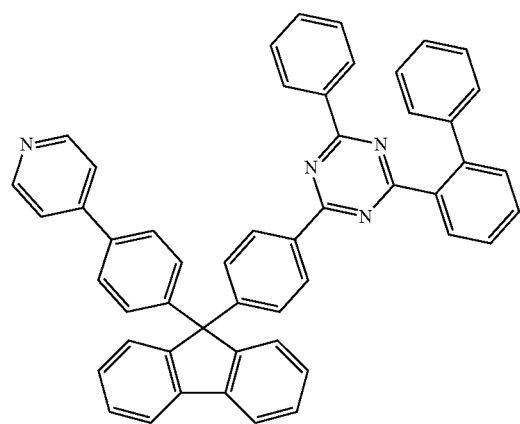
cpd 73
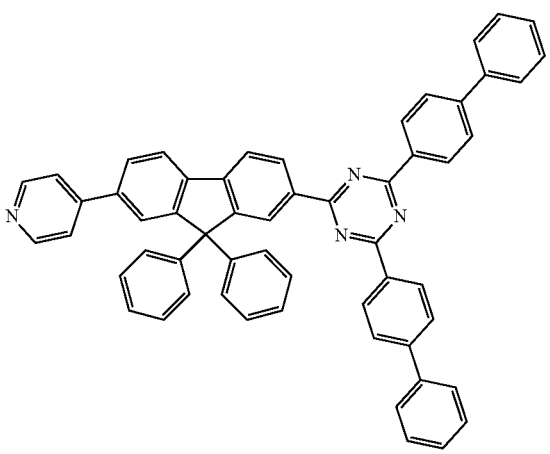

cpd 74
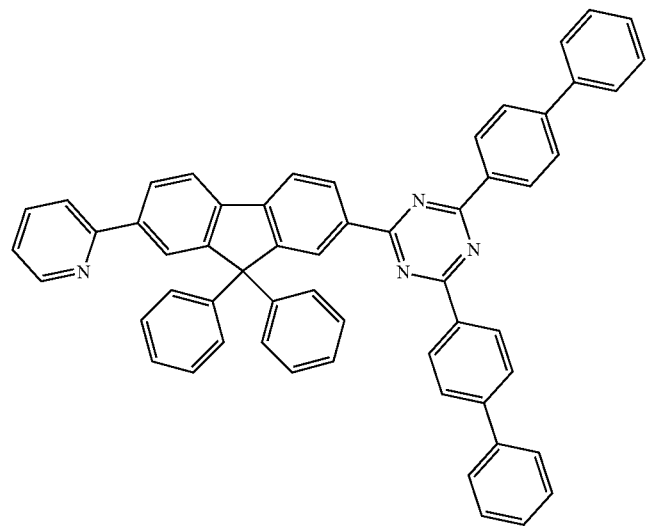
cpd 75
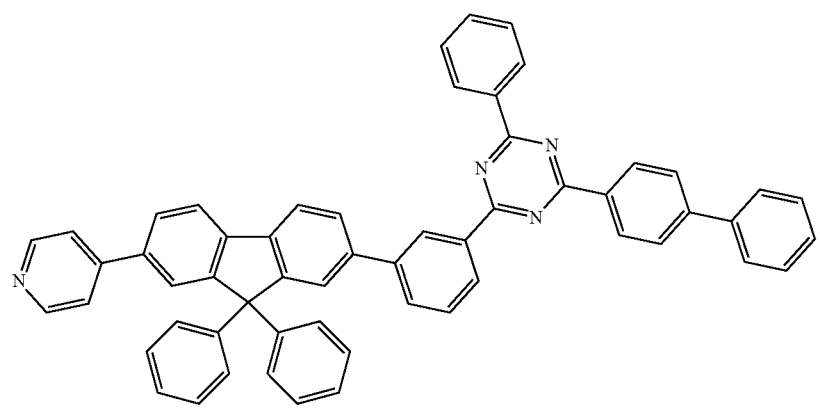
cpd 76 cpd 77
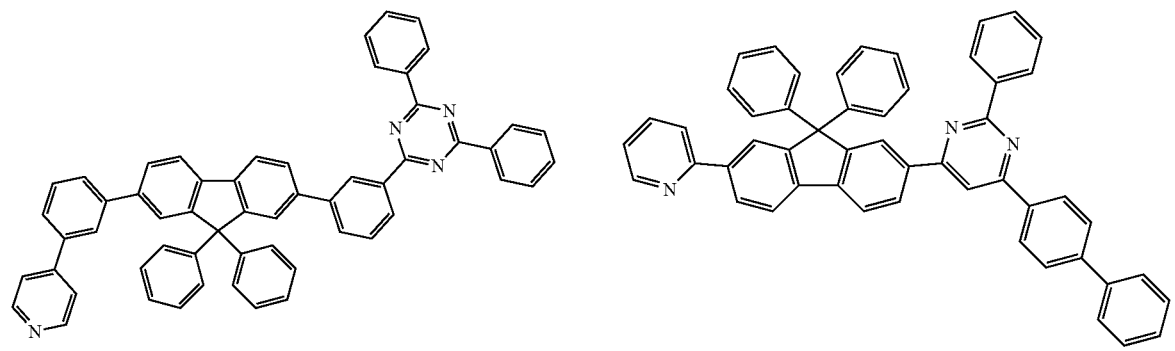

-continued
cpd 78
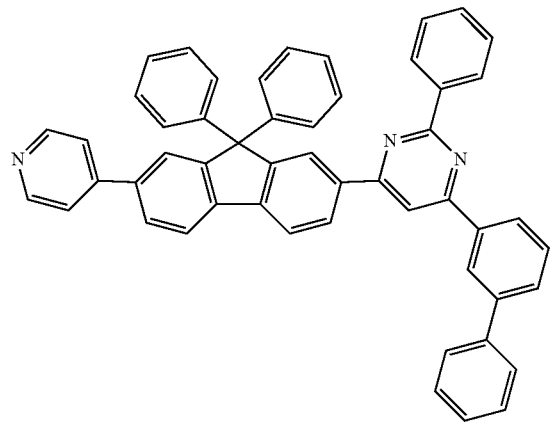
cpd 79
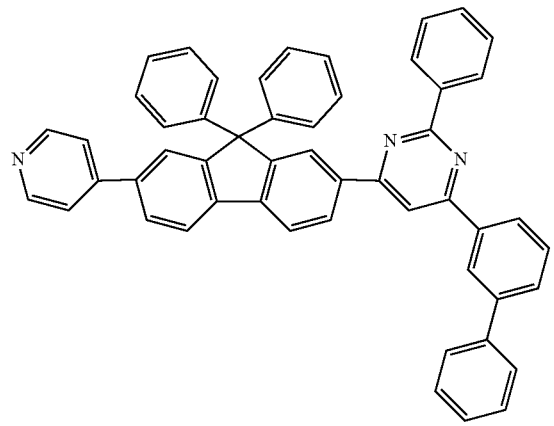
cpd 80
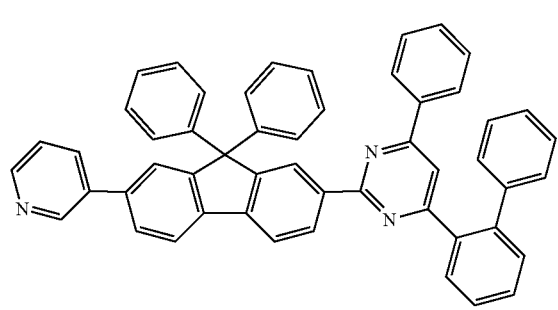
cpd 81
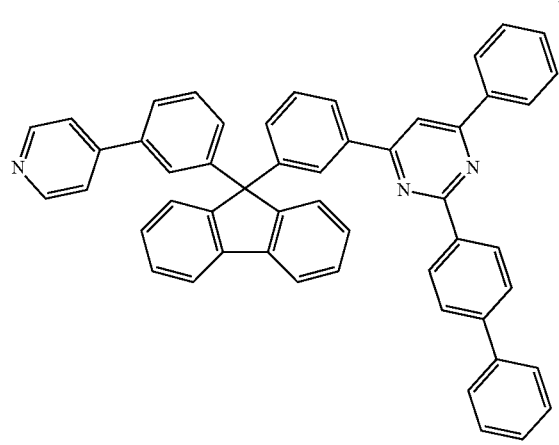
cpd 82
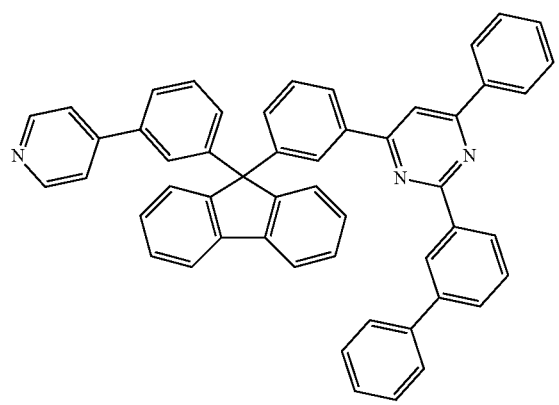
cpd 83
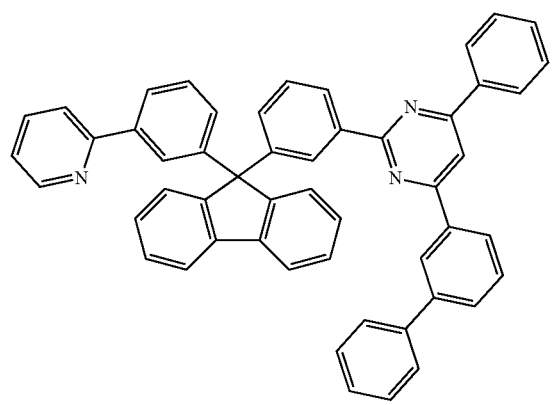
cpd 84
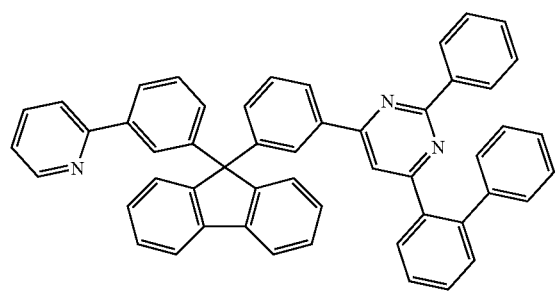
cpd 85
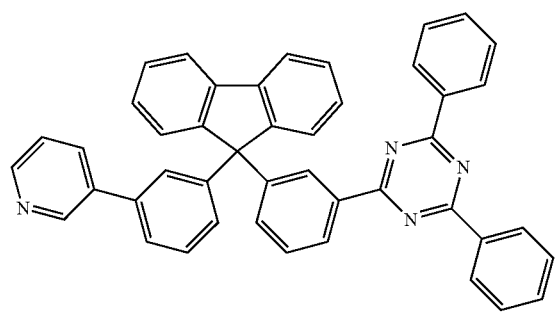

-continued
cpd 86
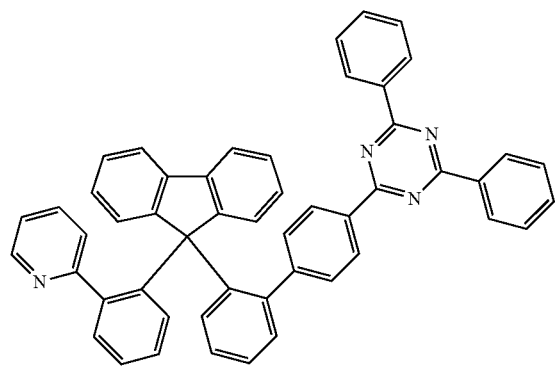
cpd 87
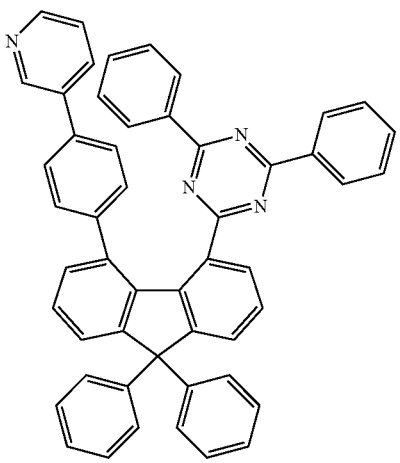
cpd 88
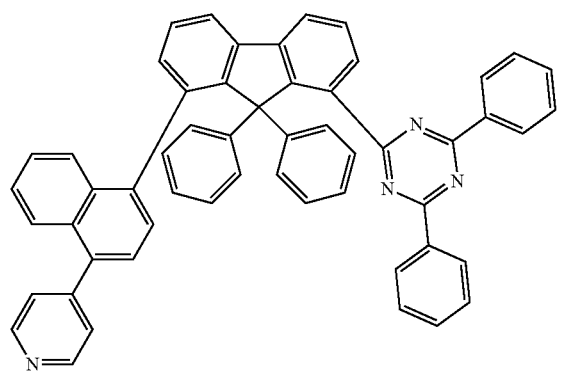
cpd 89
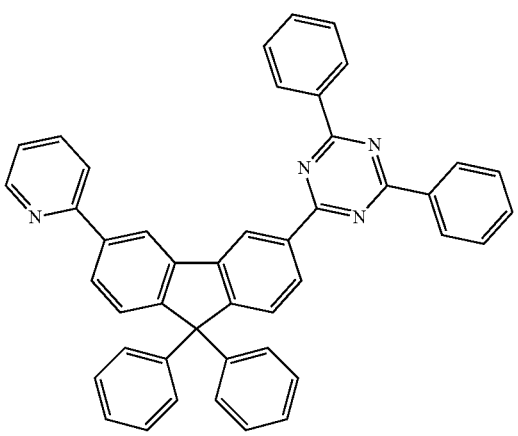
cpd 90
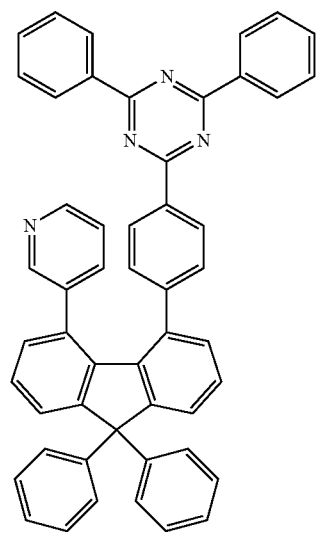
cpd 91
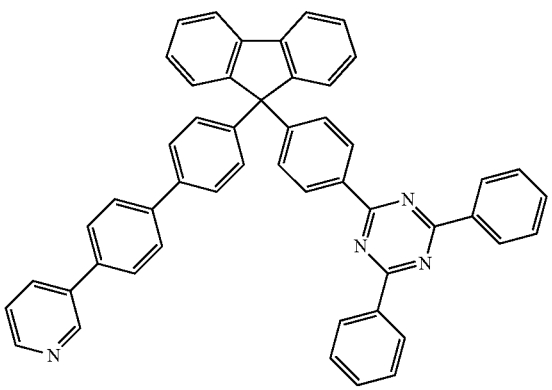

-continued
cpd 92
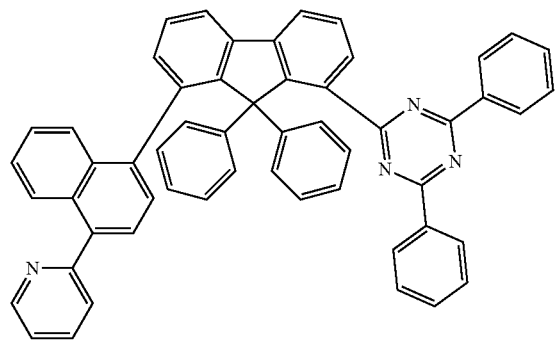
cpd 93
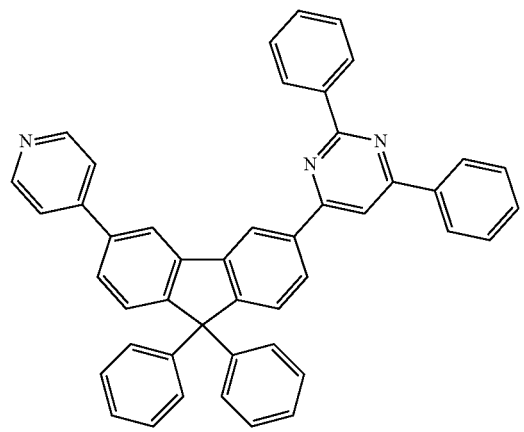
cpd 94
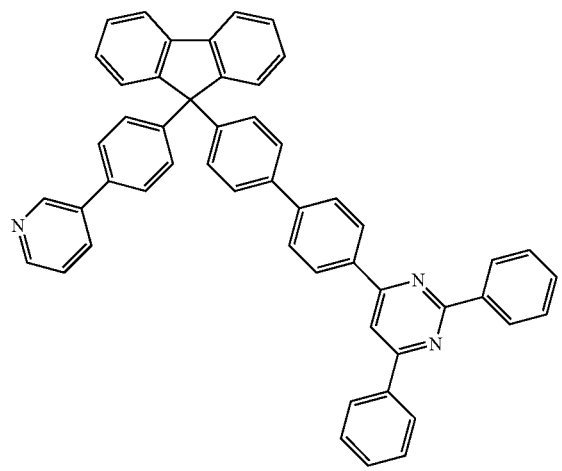
cpd 95
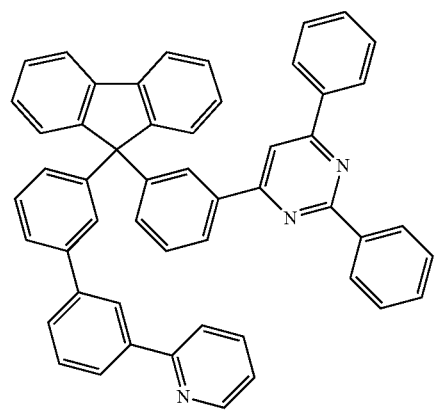
cpd 96
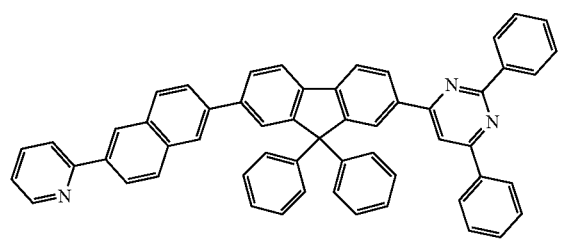
cpd 97
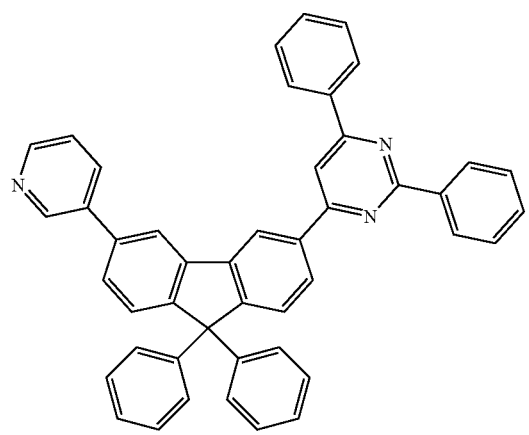

-continued
cpd 98
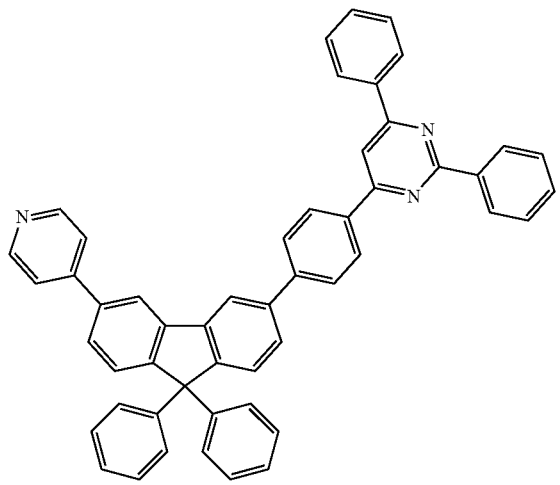
cpd 99
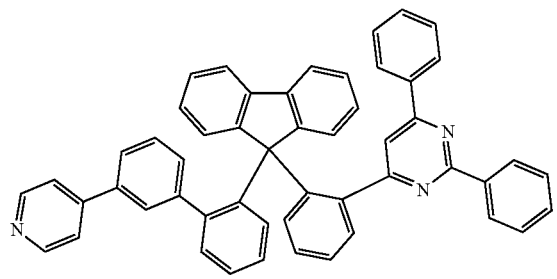
cpd 100
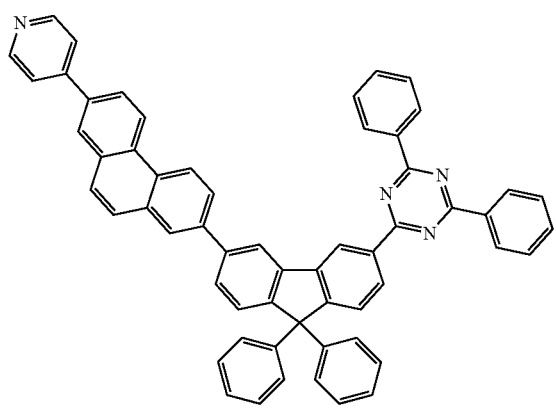
cpd 101
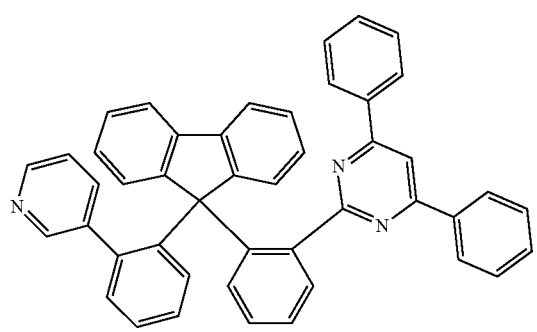
cpd 102
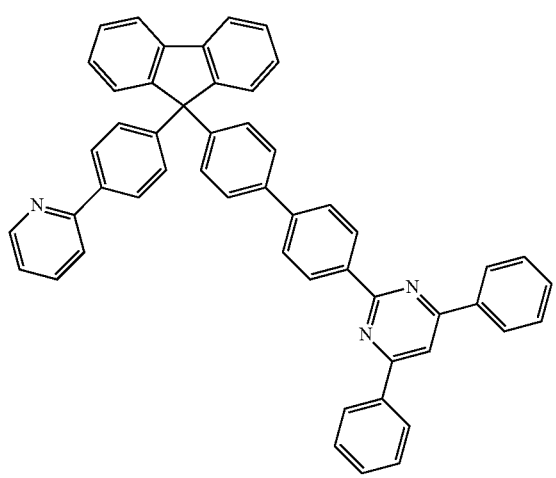
cpd 103
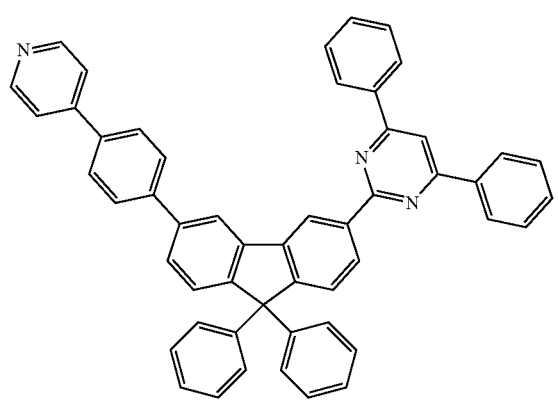

-continued cpd 104

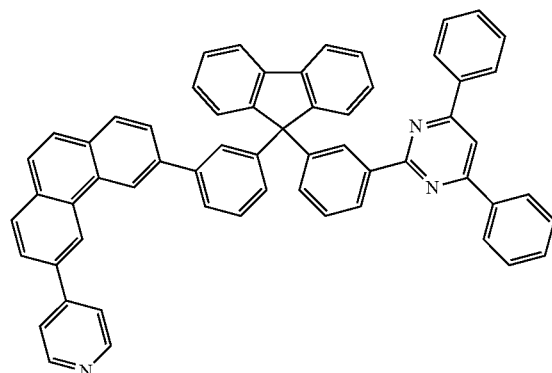

cpd 105

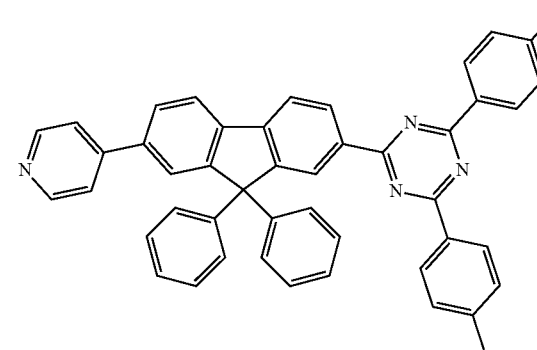

cpd 106

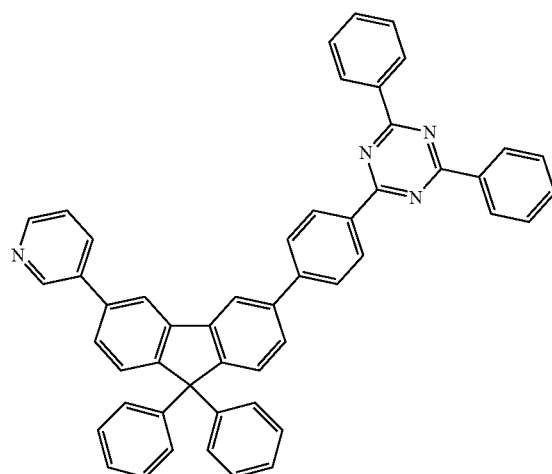

cpd 107

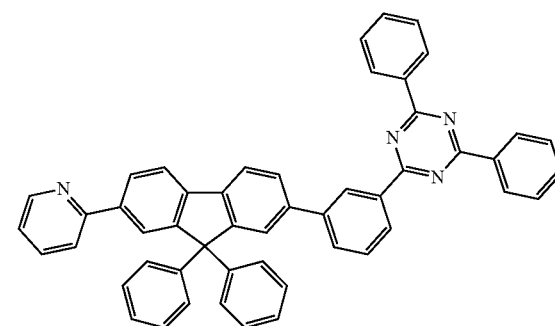

cpd 108

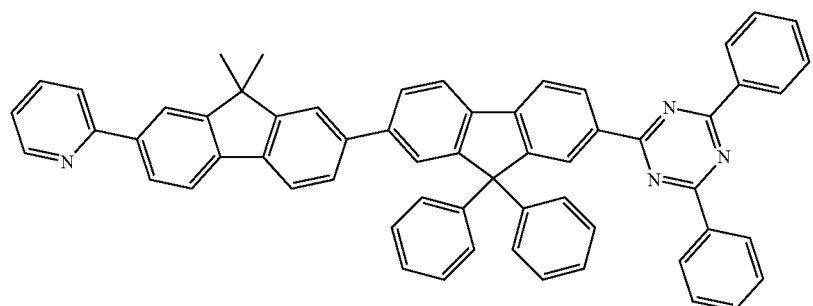

An organic light emitting device according to the present disclosure includes a first electrode; a second electrode provided opposite to the first electrode; and a light emitting layer provided between the first electrode and the second electrode, wherein the light emitting layer includes the fluorene derivative of Chemical Formula 1.

According to one embodiment of the present specification, the first electrode can be an anode; and the second electrode can be a cathode.

The organic light emitting device of the present disclosure can be manufactured using common organic light emitting device manufacturing methods and materials, except that one or more organic material layers are formed using the above-described compound.

The organic material layer of the organic light emitting device of the present disclosure can be formed in a single layer structure, but can be formed in a multilayer structure in which two or more organic material layers are laminated.

In one embodiment of the present disclosure, the organic material layer includes an electron injection layer, an electron transfer layer, or an electron injection and transfer layer, and the electron injection layer, the electron transfer layer, or the electron injection and transfer layer can include the fluorene derivative of Chemical Formula 1.

In one embodiment of the present disclosure, the organic material layer includes an electron control layer, and the electron control layer can include the fluorene derivative of Chemical Formula 1.

In one embodiment of the present disclosure, the organic material layer includes a hole injection layer or a hole transfer layer, and the hole injection layer or the hole transfer layer can include the fluorene derivative of Chemical Formula 1.

In one embodiment of the present disclosure, the organic material layer includes a hole control layer, and the hole control layer can include the fluorene derivative of Chemical Formula 1.

In one embodiment of the present disclosure, the organic material layer includes a light emitting layer, and the light emitting layer can include the fluorene derivative of Chemical Formula 1.

According to one embodiment of the present specification, the organic material layer can use LiQ together with the compound of Chemical Formula 1.

According to one embodiment of the present specification, the organic material layer can use LiQ together with the compound of Chemical Formula 1, and different hole transfer layer materials can be used at the front or the back of the organic material layer using LiQ together with the compound of Chemical Formula 1.

According to one embodiment of the present specification, the electron injection layer, the electron transfer layer, or the electron injection and transfer layer can use LiQ together with the compound of Chemical Formula 1 in a weight ratio of 3:7 to 7:3.

For examples, the organic light emitting device of the present disclosure can have a structure as illustrated in FIG. 1, however, the structure is not limited thereto.

FIG. 1 illustrates a structure of the organic light emitting device in which a first electrode (2), an organic material layer (3) and a second electrode (4) are consecutively laminated on a substrate (1).

FIG. 2 illustrates a structure of the organic light emitting device in which a first electrode (2), an organic material layer (3), a light emitting layer (5), an electron injection and transfer layer (6) and a second electrode (4) are consecutively laminated on a substrate (1). In one embodiment of the present disclosure, the organic material layer including the compound of Chemical Formula 1 includes at least one of an electron injection layer, an electron r layer, and a layer carrying out electron injection and electron transfer at the same time, and at least one of the layers can include the compound of Chemical Formula 1.

For example, the organic light emitting device according to the present disclosure can be manufactured by forming an anode on a substrate by depositing metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer and an organic material layer including the compound of Chemical Formula 1 thereon, and then depositing a material capable of being used as a cathode thereon. In addition to such a method, the organic light emitting device can also be manufactured by consecutively depositing a cathode material, an organic material layer and an anode material on a substrate.

As the first electrode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as Zno:Al or SnO:Sb; conductive polymers such as poly [3,4-(ethylene-1,2-dioxy)compound] (PEDT), polypyrrole and polyaniline, but are not limited thereto.

As the second electrode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO/Al, and the like, but are not limited thereto.

The hole injection material is a material capable of favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and poly compound-based conductive polymers, and the like, but are not limited thereto.

The hole transfer material is a material capable of receiving holes from an anode or a hole injection layer, and moving the holes to a light emitting layer, and materials having high mobility for the holes are suited. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and materials having favorable quantum efficiency for fluorescence or phosphorescence are preferred. Specific examples thereof include 8-hydroxy-quinoline aluminum complexes (Alq$_3$), carbazole series compounds, dimerized styryl compounds, BAlq, 10-hydroxy-benzoquinoline-metal compounds, benzoxazole, benzothiazole and benzimidazole series compounds; poly(p-phenylenevinylene) (PPV) series polymers, spiro compounds, polyfluorene, rubrene, and the like, but are not limited thereto.

Methods for preparing the fluorene derivative, and methods for manufacturing an organic light emitting device including the same will be specifically described in the following preparation examples and examples. However, the following preparation examples and examples are for illustrative purposes only, and the scope of the present specification is not limited thereby.

PREPARATION EXAMPLES

Preparation Example 1: Preparation of Compound 2

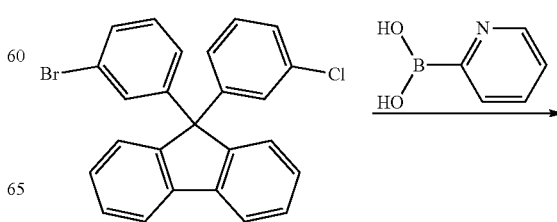

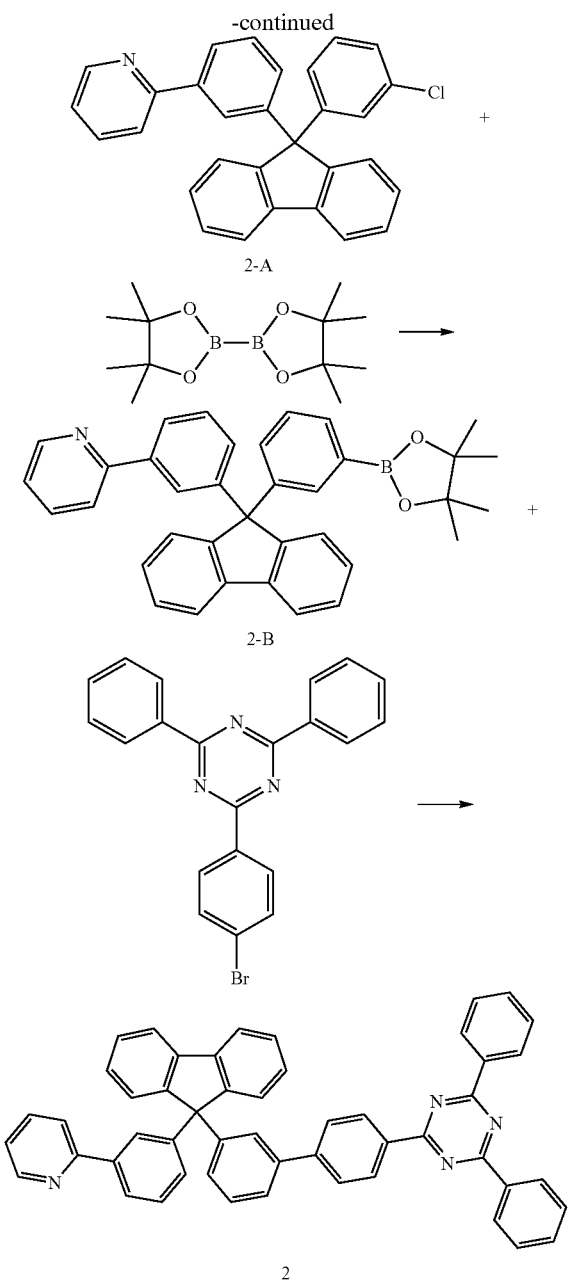

2-A

2-B

2

Under a nitrogen stream, 9-(3-bromophenyl)-9-(3-chlorophenyl)-9H-fluorene (20 g, 46.3 mmol), 2-pyridyl boronic acid (5.7 g, 46.3 mmol) and potassium carbonate (12.8 g, 92.6 mmol) were introduced to tetrahydrofuran (THF) (200 mL), and the result was stirred while heating. Tetrakis(triphenylphosphine)-palladium (0) (1.6 g, 1.39 mmol) was introduced thereto, and the result was further stirred for 2 hours while heating. The result was cooled to room temperature, and then ethanol slurry purification was progressed thereon to prepare Compound 2-A (19 g, yield 95%).

MS: $[M+H]^+$=430

Under a nitrogen stream, Compound 2-A (21 g, 44.1 mmol), bis(pinacolato)diboron (12.3 g, 48.5 mmol) and potassium acetate (8.6 g, 88.2 mmol) were introduced to dioxane (200 mL), and the result was stirred while heating. Bis(dibenzylideneacetone)-palladium(0) (0.76 g, 1.32 mmol) and tricyclohexylphosphine (0.74 g, 2.64 mmol) were introduced thereto, and the result was further stirred for 4 hours while heating. The result was cooled to room temperature, and then ethanol slurry purification was progressed thereon to prepare Compound 2-B (28 g, yield 94%).

MS: $[M+H]^+$=546

Under a nitrogen stream, Compound 2-B (28 g, 41.4 mmol), 2-(4-bromophenyl)-4,6-diphenyl-1,3,5-triazine (16.1 g, 41.4 mmol) and potassium carbonate (11.4 g, 82.8 mmol) were introduced to tetrahydrofuran (THF) (200 mL), and the result was stirred while heating. Tetrakis(triphenylphosphine)palladium(0) (1.44 g, 1.24 mmol) was introduced thereto, and the result was further stirred for 3 hours while heating. The result was cooled to room temperature, and then ethanol slurry purification was progressed thereon to prepare Compound 2 (25 g, yield 93%).

MS: $[M+H]^+$=651

Preparation Example 2: Preparation of Compound 5

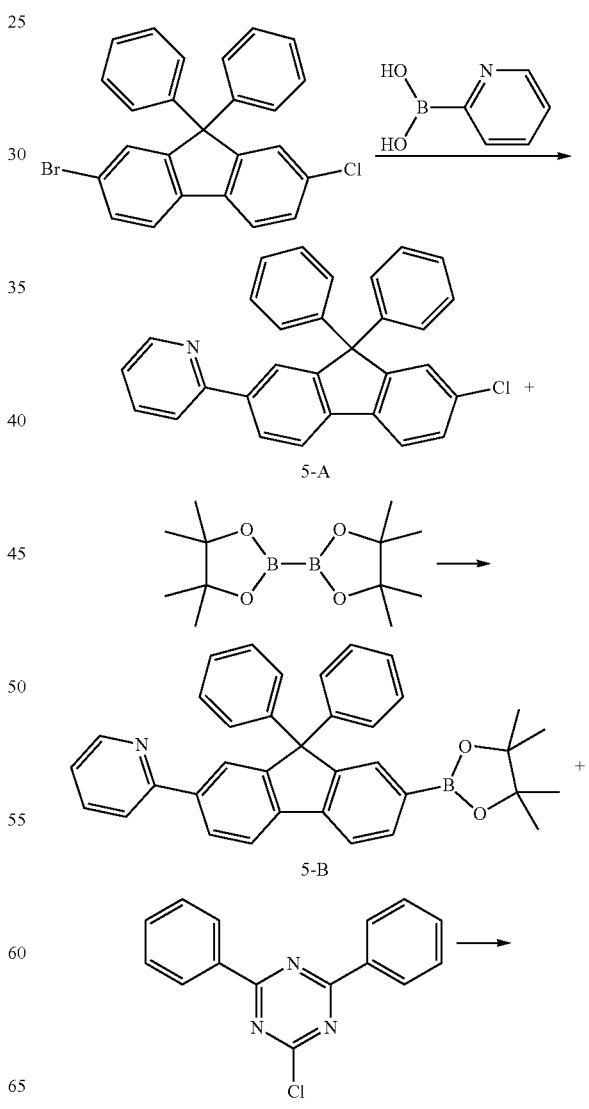

5-A

5-B

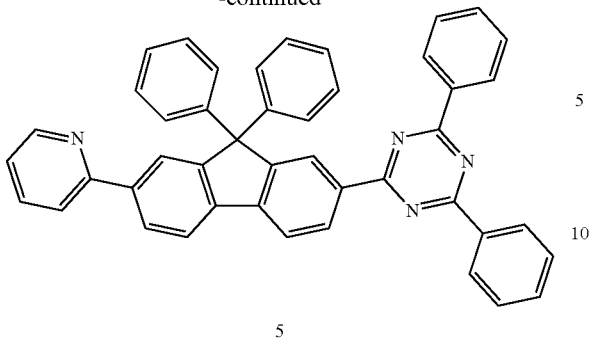

5

Compound 5-A was prepared in the same manner as in the preparation of Compound 2-A except that 2-bromo-7-chloro-9,9-diphenyl-9H-fluorene was used instead of 9-(3-bromophenyl)-9-(3-chlorophenyl)-9H-fluorene.

MS: [M+H]⁺=430

Compound 5-B was prepared in the same manner as in the preparation of Compound 2-B except that Compound 5-A was used instead of Compound 2-A.

MS: [M+H]⁺=522

Compound 5 was prepared in the same manner as in the preparation of Compound 2, except that Compound 5-B was used instead of Compound 2-B and 2-chloro-4,6-diphenyl-1,3,5-triazine was used instead of 2-(4-bromophenyl)-4,6-diphenyl-1,3,5-triazine.

MS: [M+H]⁺=627

Preparation Example 3: Preparation of Compound 6

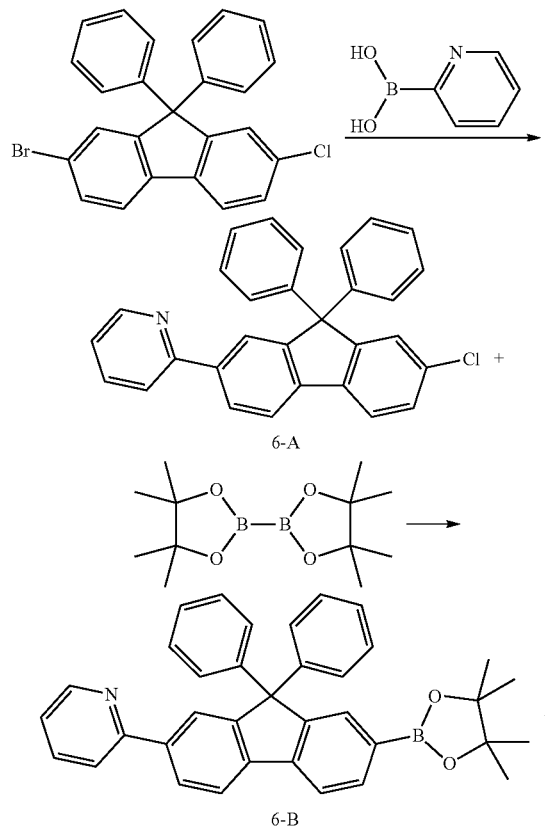

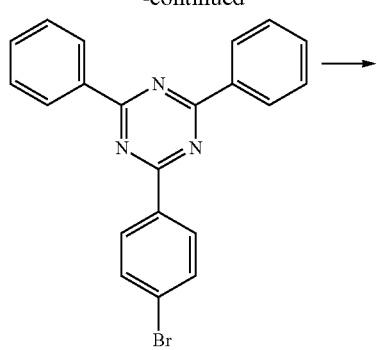

6

Compound 6 was prepared in the same manner as in the preparation of Compound 5 except that 2-(4-bromophenyl)-4,6-diphenyl-1,3,5-triazine was used instead of 2-chloro-4,6-diphenyl-1,3,5-triazine.

MS: [M+H]⁺=703

Preparation Example 4: Preparation of Compound 13

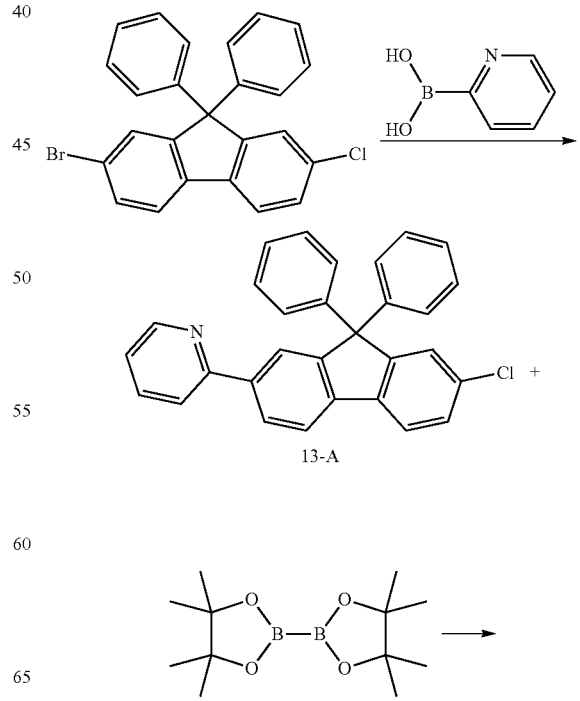

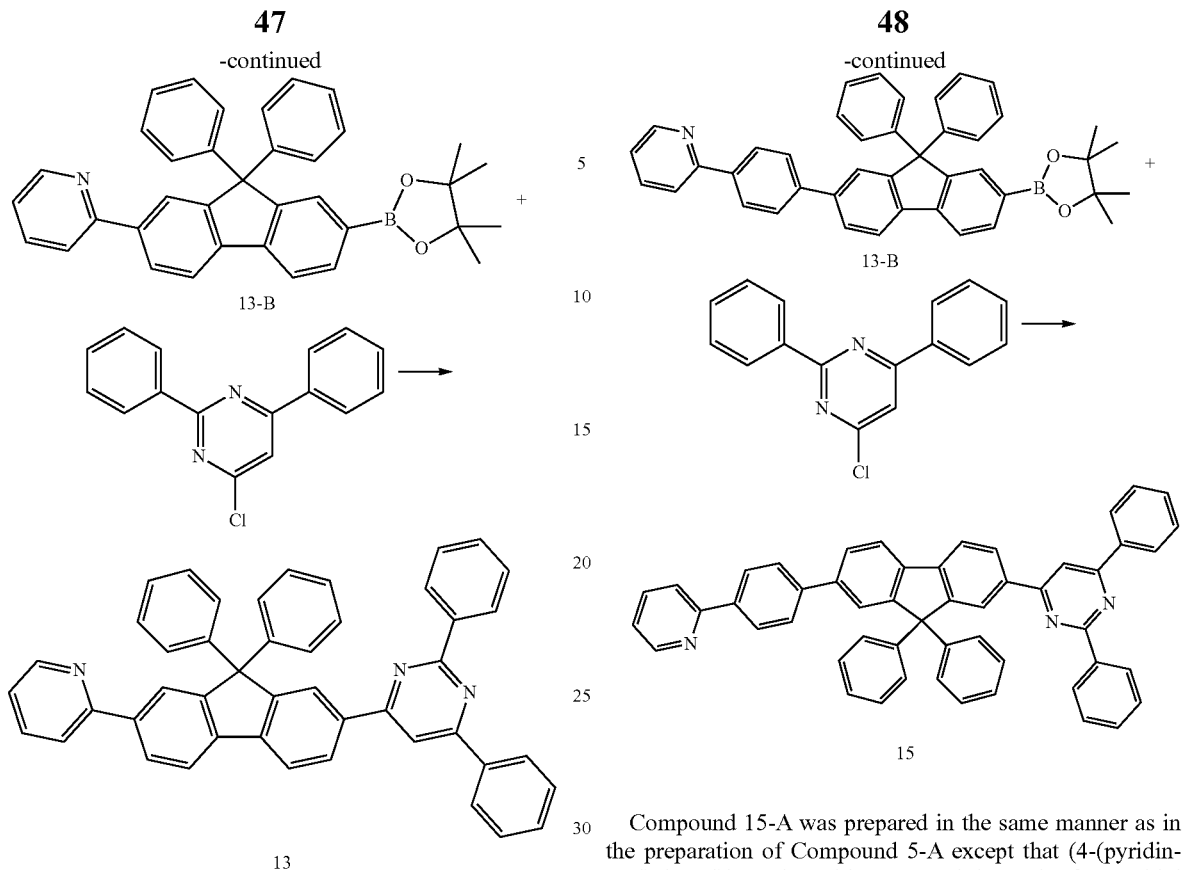

Compound 13 was prepared in the same manner as in the preparation of Compound 5, except that 4-chloro-2,6-diphenylpyrimidine was used instead of 2-chloro-4,6-diphenyl-1,3,5-triazine.

MS: [M+H]$^+$=626

Preparation Example 5: Preparation of Compound 15

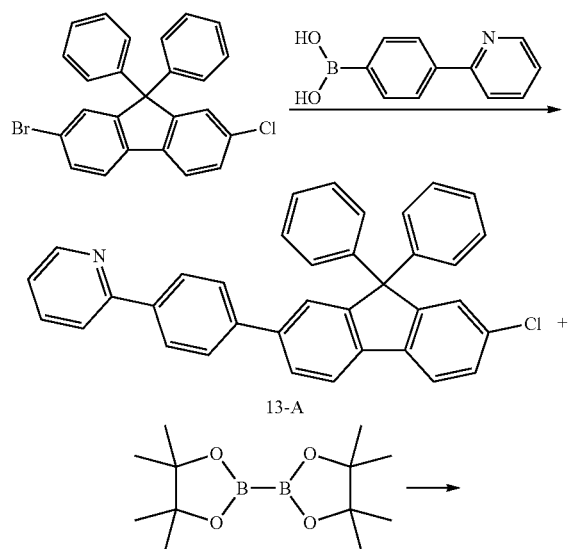

Compound 15-A was prepared in the same manner as in the preparation of Compound 5-A except that (4-(pyridin-2-yl)phenyl)boronic acid was used instead of 2-pyridyl boronic acid.

MS: [M+H]$^+$=506

Compound 15-B was prepared in the same manner as in the preparation of Compound 5-B except that Compound 15-A was used instead of Compound 5-A.

MS: [M+H]$^+$=598

Compound 15 was prepared in the same manner as in the preparation of Compound 5, except that Compound 15-B was used instead of Compound 5-B and 4-chloro-2,6-diphenylpyrimidine was used instead of 2-chloro-4,6-diphenyl-1,3,5-triazine.

MS: [M+H]$^+$=702

Preparation Example 6: Preparation of Compound 18

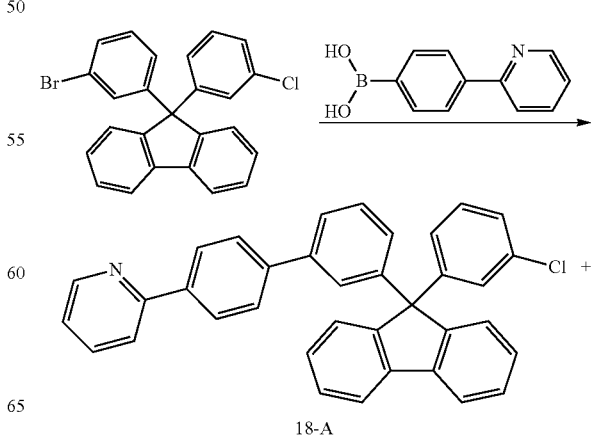

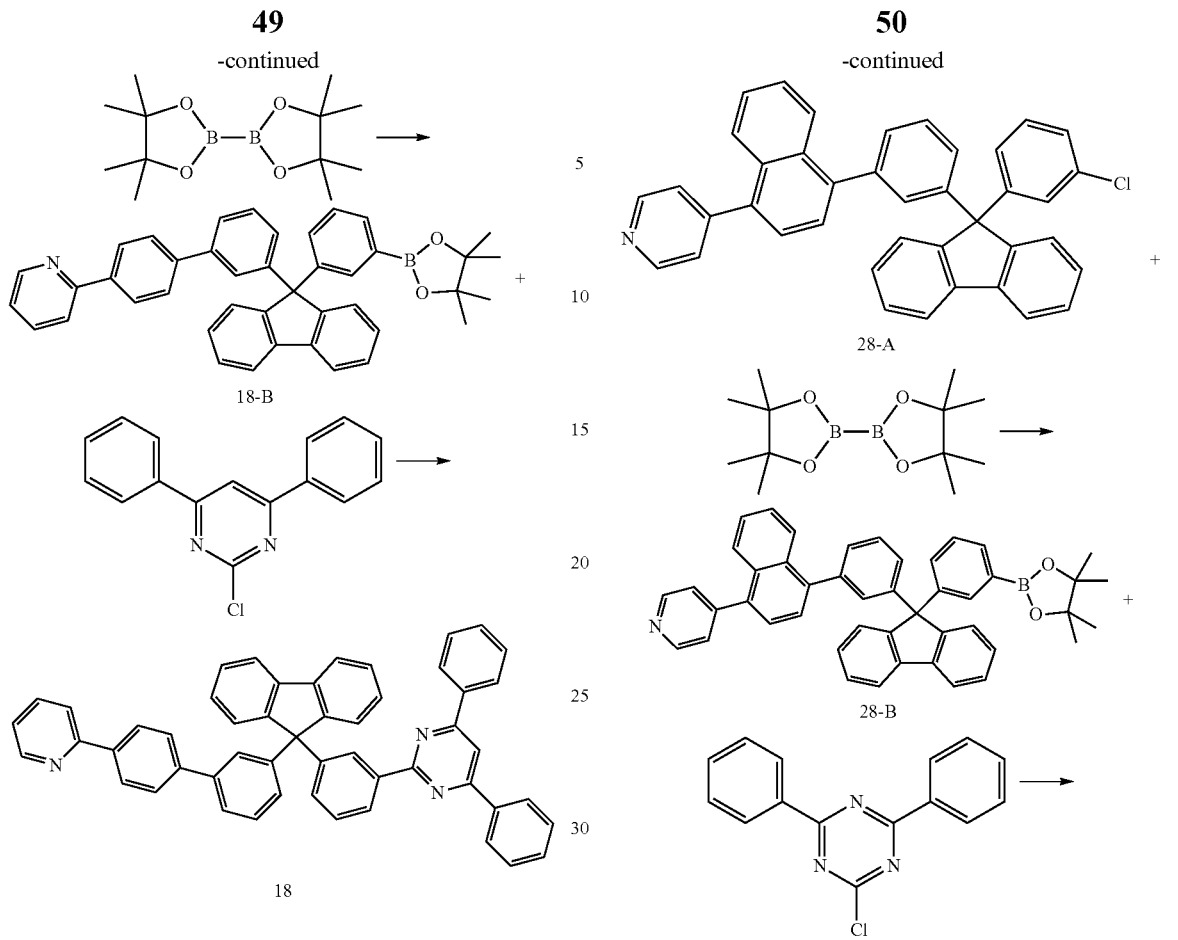

Compound 18-A was prepared in the same manner as in the preparation of Compound 15-A except that 9-(3-bromophenyl)-9-(3-chlorophenyl)-9H-fluorene was used instead of 2-bromo-7-chloro-9,9-diphenyl-9H-fluorene.

MS: [M+H]$^+$=506

Compound 18-B was prepared in the same manner as in the preparation of Compound 15-B except that Compound 18-A was used instead of Compound 15-A.

MS: [M+H]$^+$=598

Compound 18 was prepared in the same manner as in the preparation of Compound 15, except that Compound 18-B was used instead of Compound 15-B and 2-chloro-4,6-diphenylpyrimidine was used instead of 4-chloro-2,6-diphenylpyrimidine.

MS: [M+H]$^+$=702

Preparation Example 7: Preparation of Compound 28

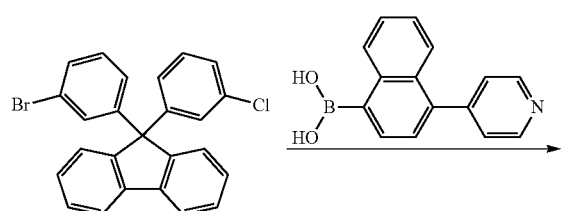

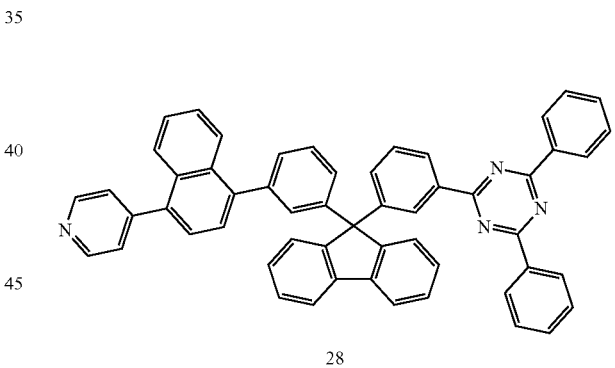

Compound 28-A was prepared in the same manner as in the preparation of Compound 18-A except that (4-(pyridin-4-yl)naphthalen-1-yl)boronic acid was used instead of (4-(pyridin-2-yl)phenyl)boronic acid.

MS: [M+H]$^+$=556

Compound 28-B was prepared in the same manner as in the preparation of Compound 18-B except that Compound 28-A was used instead of Compound 18-A.

MS: [M+H]$^+$=648

Compound 28 was prepared in the same manner as in the preparation of Compound 18, except that Compound 28-B was used instead of Compound 18-B and 2-chloro-4,6-diphenyl-1,3,5-triazine was used instead of 2-chloro-4,6-diphenylpyrimidine.

MS: [M+H]$^+$=753

Preparation Example 8: Preparation of Compound 30

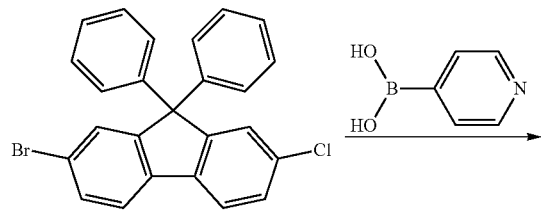

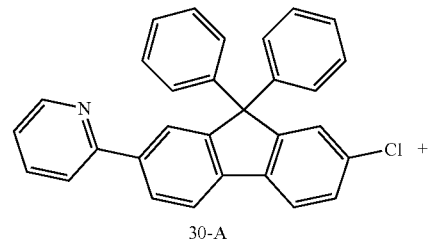

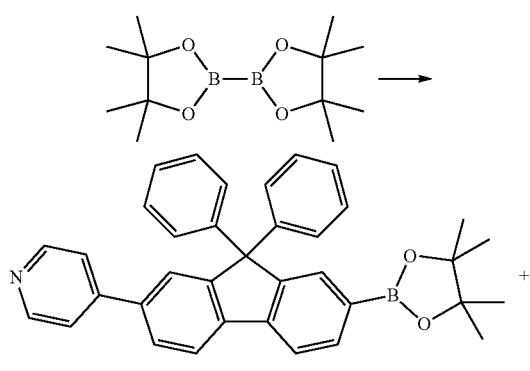

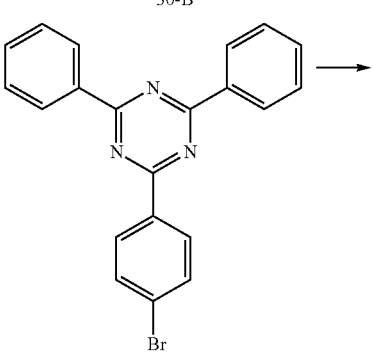

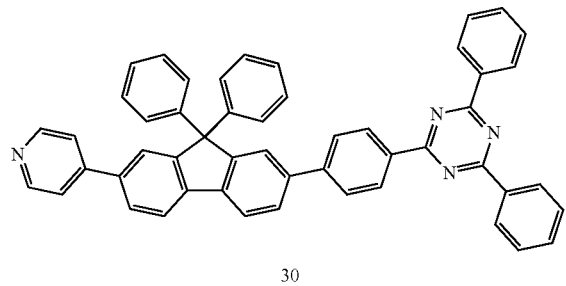

30

Compound 30-A was prepared in the same manner as in the preparation of Compound 6-A except that 4-pyridyl boronic acid was used instead of 2-pyridyl boronic acid.

MS: [M+H]$^+$=430

Compound 30-B was prepared in the same manner as in the preparation of Compound 6-B except that Compound 30-A was used instead of Compound 6-A.

MS: [M+H]$^+$=522

Compound 30 was prepared in the same manner as in the preparation of Compound 6 except that Compound 30-B was used instead of Compound 6-B.

MS: [M+H]$^+$=703

Preparation Example 9: Preparation of Compound 31

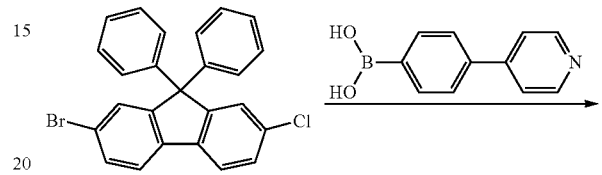

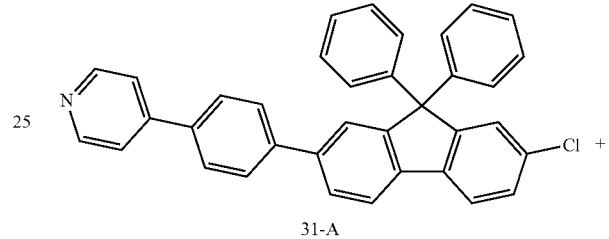

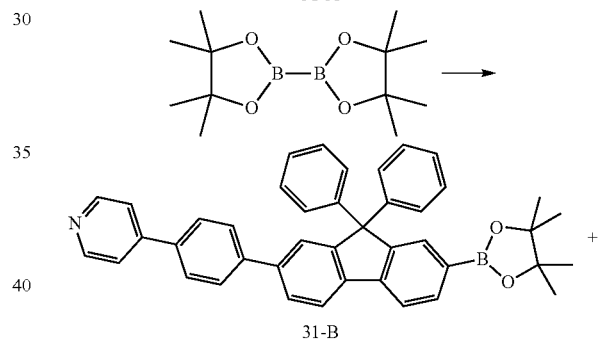

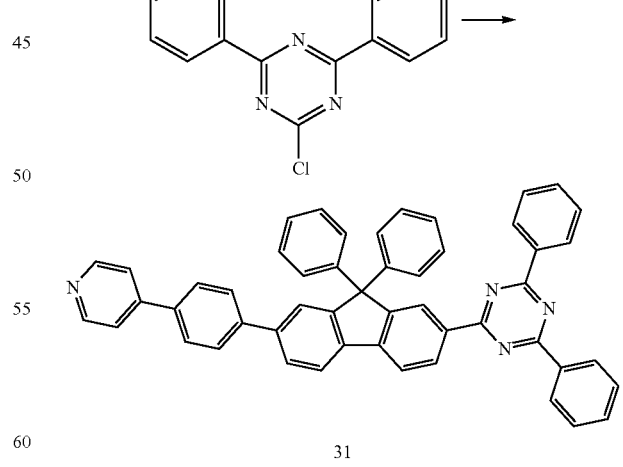

31

Compound 31-A was prepared in the same manner as in the preparation Compound 15-A except that (4-(pyridin-4-yl)phenyl)boronic acid was used instead of (4-(pyridin-2-yl)phenyl)boronic acid.

MS: [M+H]$^+$=506

Compound 31-B was prepared in the same manner as in the preparation of Compound 15-B except that Compound 31-A was used instead of Compound 15-A.

MS: [M+H]⁺=598

Compound 31 was prepared in the same manner as in the preparation of Compound 15, except that Compound 31-B was used instead of Compound 15-B and 2-chloro-4,6-diphenyl-1,3,5-triazine was used instead of 4-chloro-2,6-diphenylpyrimidine.

MS: [M+H]⁺=703

Preparation Example 10: Preparation of Compound 52

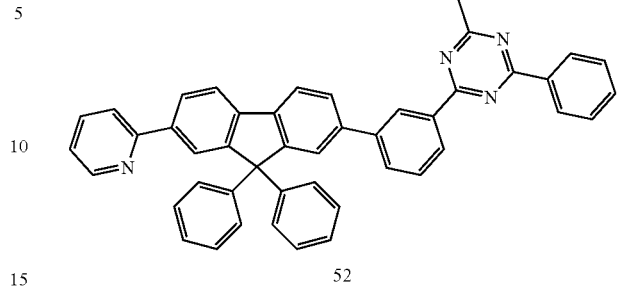

52

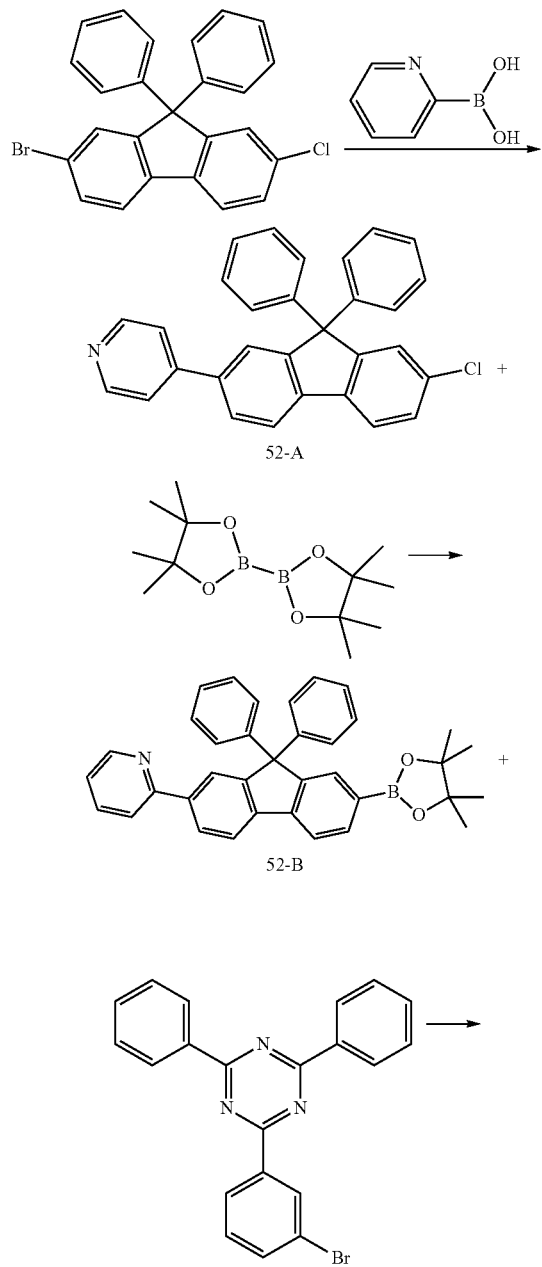

Compound 52 was prepared in the same manner as in the preparation of Compound 5 except that 2-(3-bromophenyl)-4,6-diphenyl-1,3,5-triazine was used instead of 2-chloro-4,6-diphenyl-1,3,5-triazine.

MS: [M+H]⁺=703

Preparation Example 11: Preparation of Compound 61

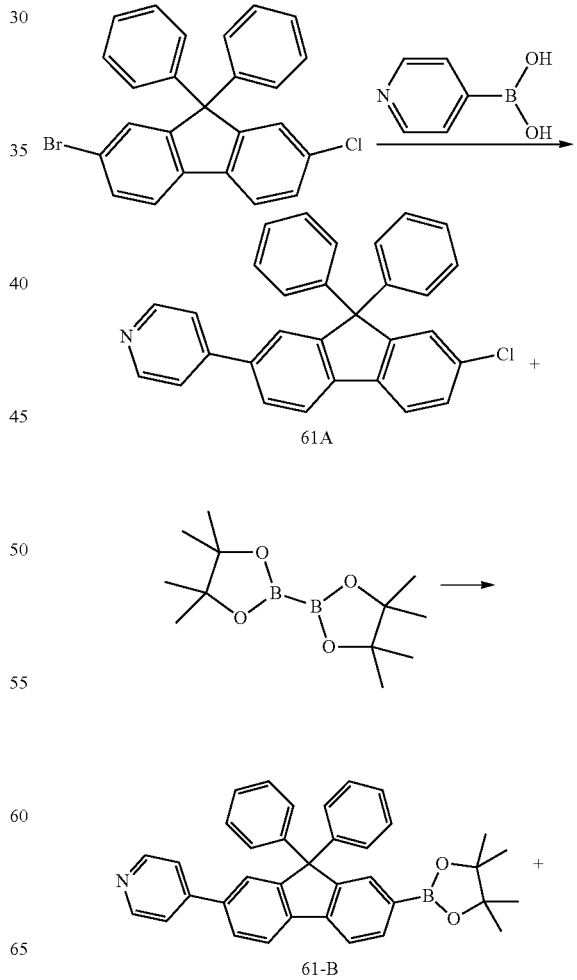

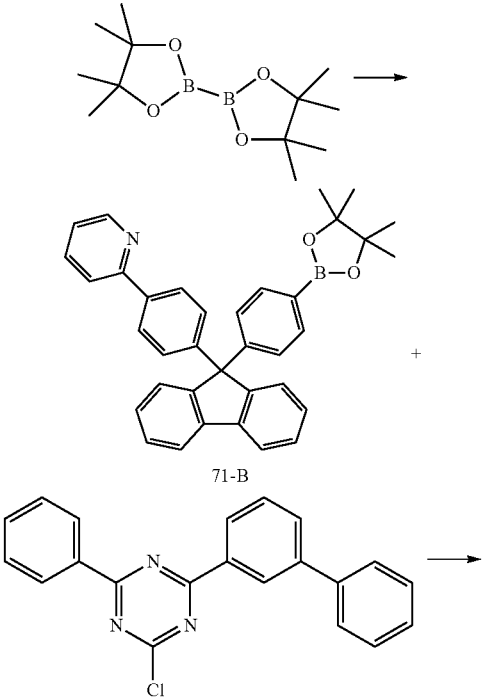

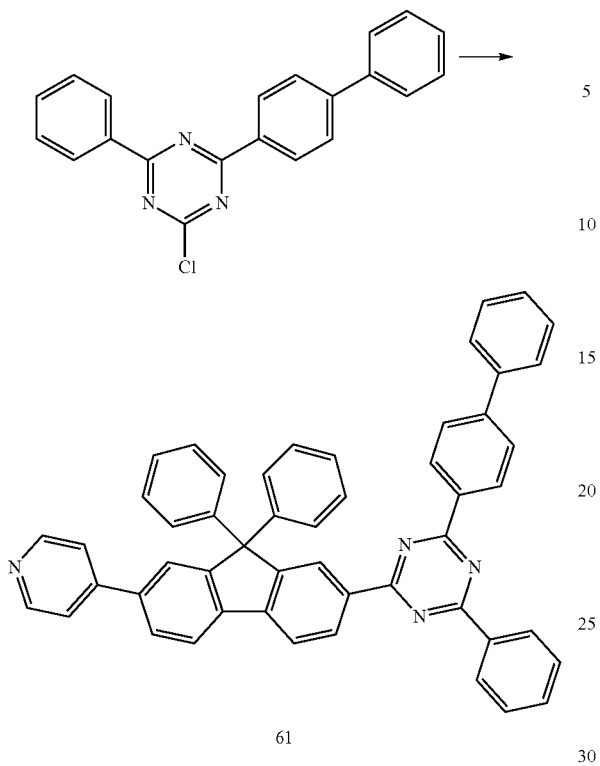

61

Compound 61 was prepared in the same manner as in the preparation of Compound 30 except that 2-([1,1'-biphenyl]-4-yl)-4-chloro-6-phenyl-1,3,5-triazine was used instead of 2-(4-bromophenyl)-4,6-diphenyl-1,3,5-triazine.

MS: [M+H]$^+$=703

Preparation Example 12: Preparation of Compound 71

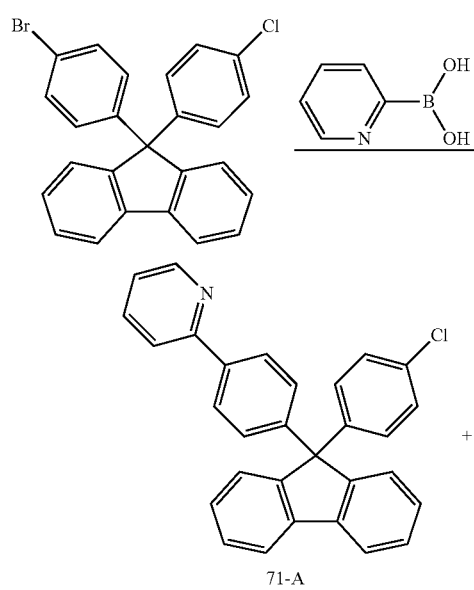

71-A

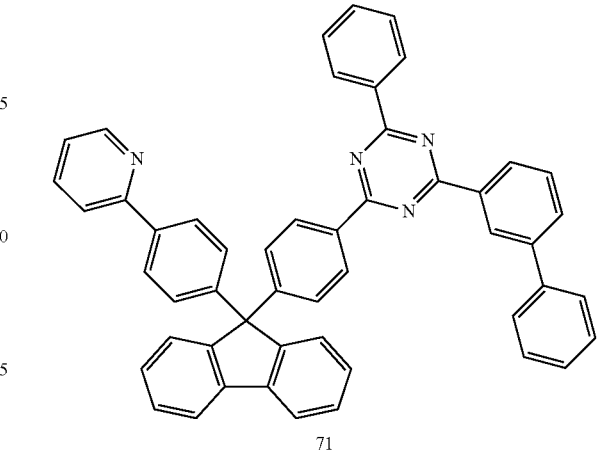

71

Compound 71-A was prepared in the same manner as in the preparation of Compound 2-A except that 9-(4-bromophenyl)-9-(4-chlorophenyl)-9H-fluorene was used instead of 9-(3-bromophenyl)-9-(3-chlorophenyl)-9H-fluorene.

MS: [M+H]$^+$=430

Compound 71-B was prepared in the same manner as in the preparation of Compound 2-B except that Compound 71-A was used instead of Compound 2-A.

MS: [M+H]$^+$=522

Compound 71 was prepared in the same manner as in the preparation of Compound 2, except that Compound 71-B was used instead of Compound 2-B and 2-([1,1'-biphenyl]-3-yl)-4-chloro-6-phenyl-1,3,5-triazine was used instead of 2-(4-bromophenyl)-4,6-diphenyl-1,3,5-triazine.

MS: [M+H]$^+$=703

Preparation Example 13: Preparation of Compound 78
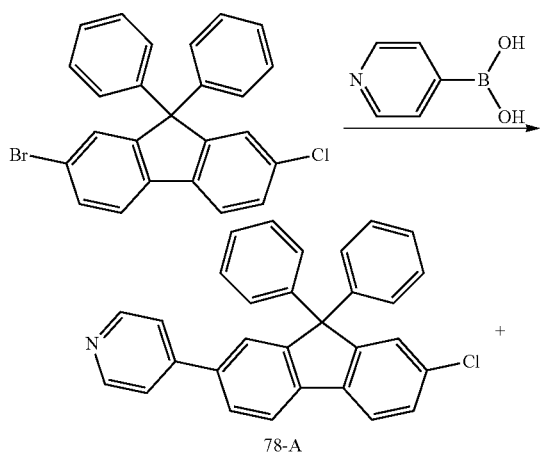
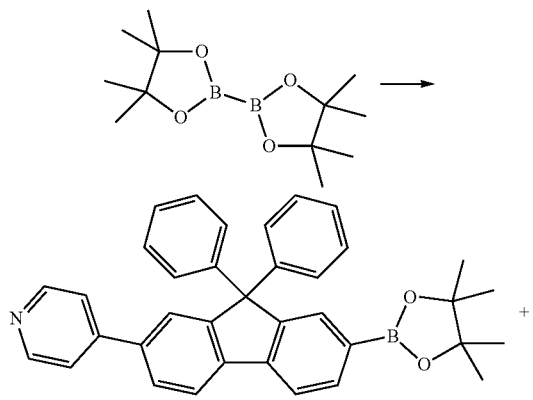
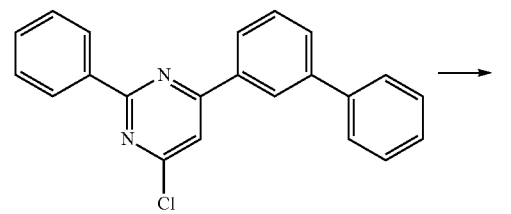
Compound 78 was prepared in the same manner as in the preparation of Compound 61, except that 4-([1,1'-biphenyl]-3-yl)-6-chloro-2-phenylpyrimidine was used instead of 2-([1,1'-biphenyl]-4-yl)-4-chloro-6-phenyl-1,3,5-triazine.
MS: [M+H]$^+$=702
Preparation Example 14: Preparation of Compound 90
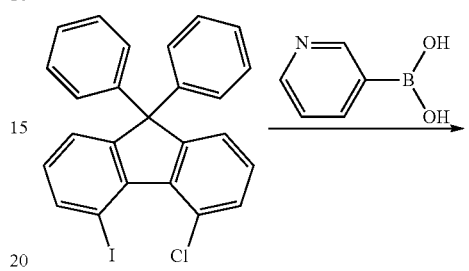
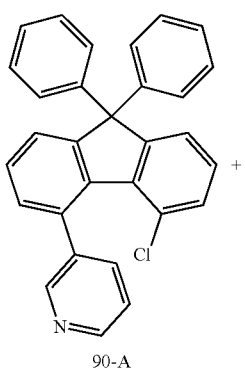
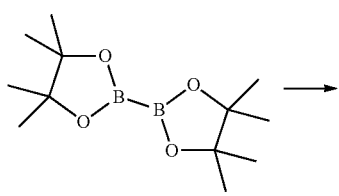
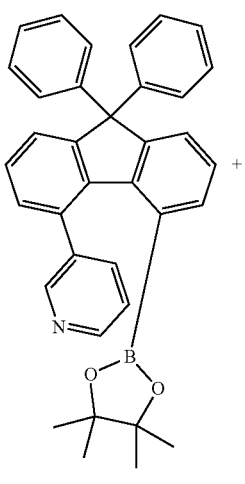

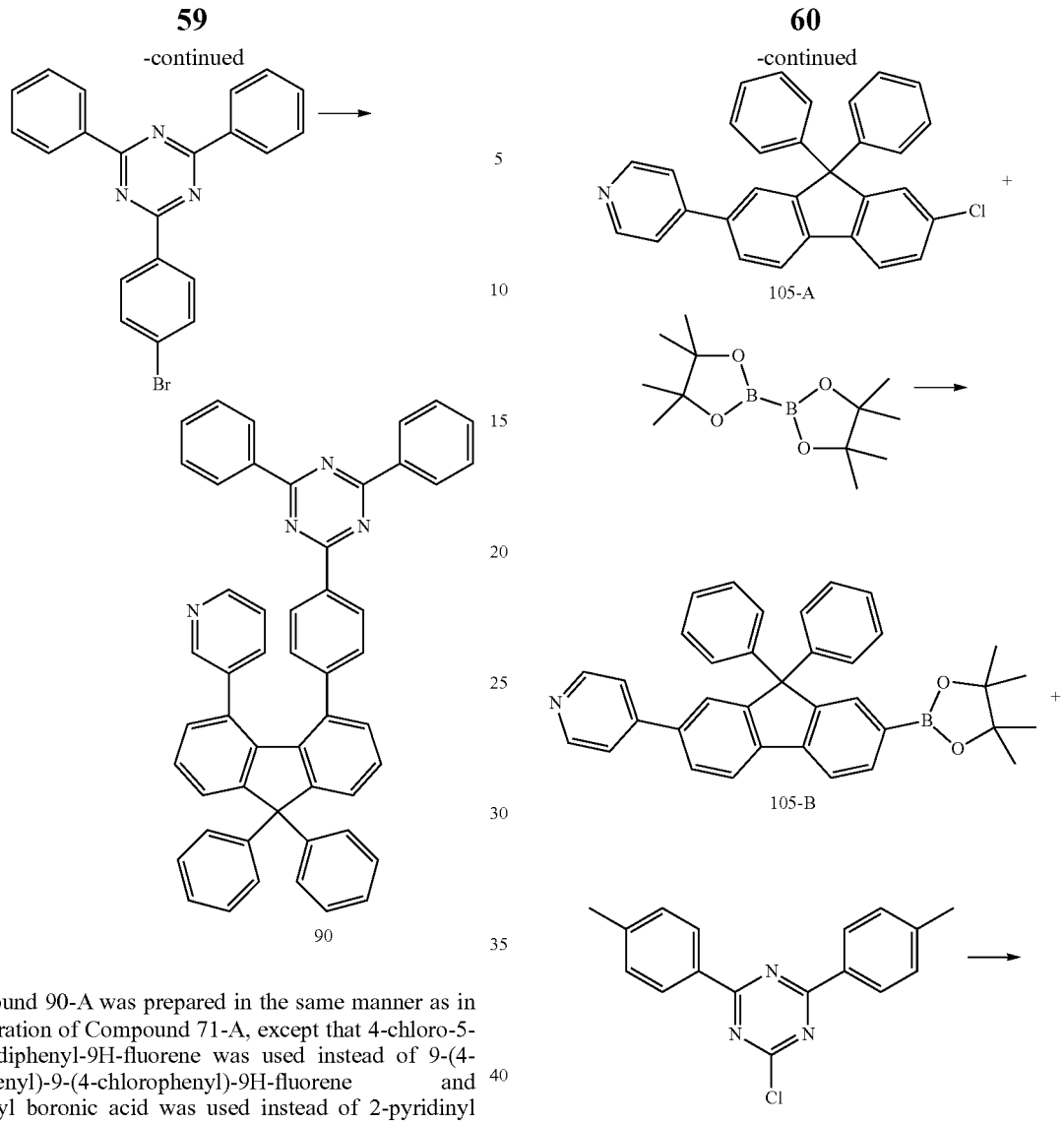

Compound 90-A was prepared in the same manner as in the preparation of Compound 71-A, except that 4-chloro-5-iodo-9,9-diphenyl-9H-fluorene was used instead of 9-(4-bromophenyl)-9-(4-chlorophenyl)-9H-fluorene and 3-pyridinyl boronic acid was used instead of 2-pyridinyl boronic acid.

MS: [M+H]$^+$=430

Compound 90-B was prepared in the same manner as in the preparation of Compound 71-B except that Compound 90-A was used instead of Compound 71-A.

MS: [M+H]$^+$=522

Compound 90 was prepared in the same manner as in the preparation of Compound 71 except that 2-(4-bromophenyl)-4,6-diphenyl-1,3,5-triazine was used instead of 2-([1,1'-biphenyl]-3-yl)-4-chloro-6-phenyl-1,3,5-triazine.

MS: [M+H]$^+$=703

Preparation Example 15: Preparation of Compound 105

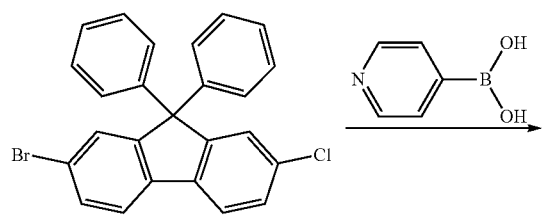

Compound 105 was prepared in the same manner as in the preparation of Compound 30 except that 2-chloro-4,6-di-p-tolyl-1,3,5-triazine was used instead of 2-(4-bromophenyl)-4,6-diphenyl-1,3,5-triazine.

MS: [M+H]$^+$=655

Preparation Example 16: Preparation of Compound 108

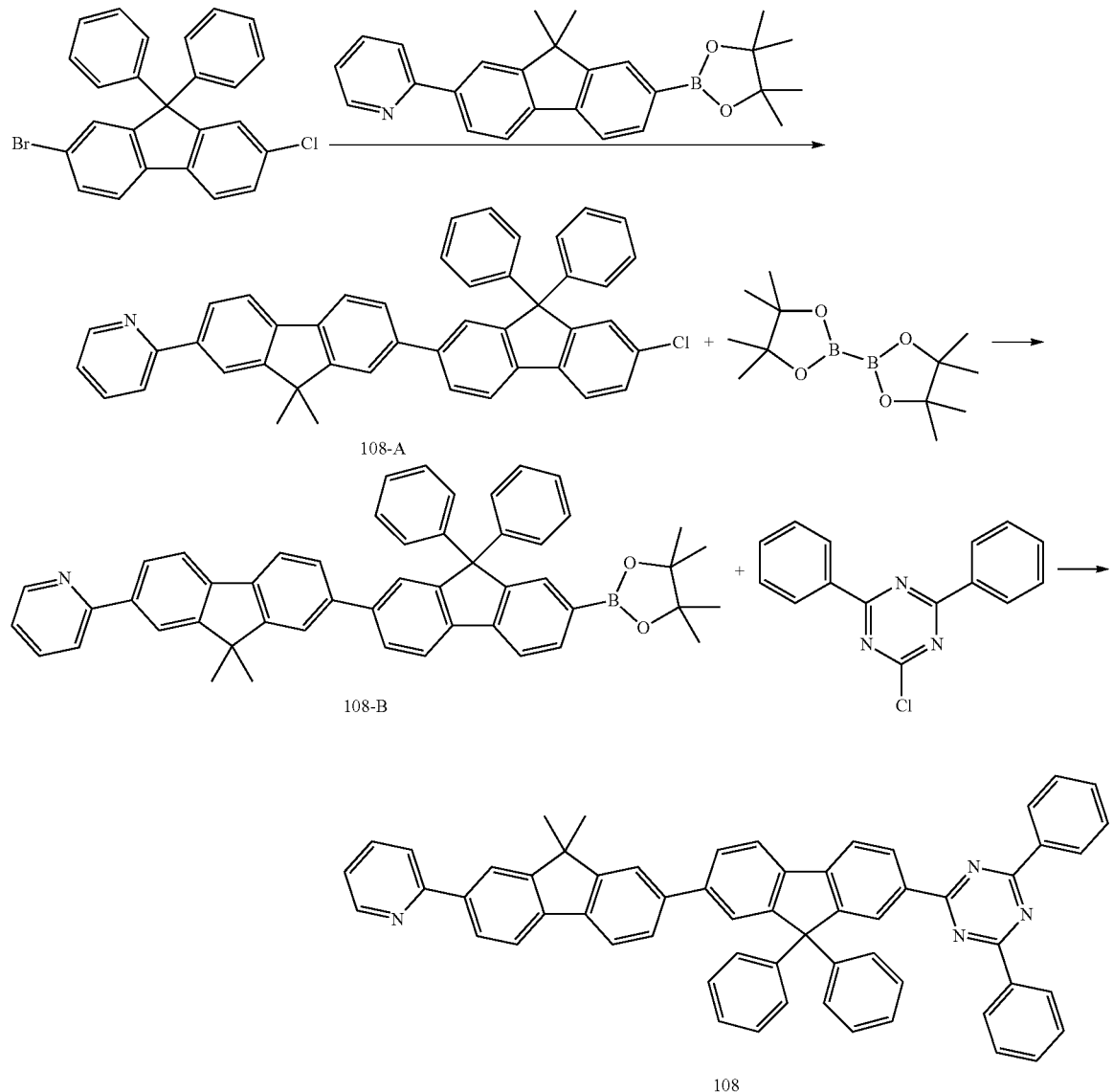

Compound 108-A was prepared in the same manner as in the preparation of Compound 5-A except that 2-(9,9-dimethyl-7-(4,4,5,5-tetramethyl-1,3,2-dioxaborolan-2-yl)-9H-fluorene-2-yl)-pyridine was used instead of 2-pyridyl boronic acid.

MS: [M+H]$^+$=622

Compound 108-B was prepared in the same manner as in the preparation of Compound 5-B except that Compound 108-A was used instead of Compound 5-A.

MS: [M+H]$^+$=714

Compound 108 was prepared in the same manner as in the preparation of Compound 5 except that Compound 108-B was used instead of Compound 5-B.

MS: [M+H]$^+$=819

EXAMPLES

Example 1

A glass substrate (corning 7059 glass) on which indium tin oxide (ITO) was coated as a thin film to a thickness of 1,000 Å placed in distilled water containing a detergent and was ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol in this order, then dried.

On the transparent ITO electrode prepared as above, a hole injection layer was formed by thermal vacuum depositing hexanitrile hexaazatriphenylene to a thickness of 500 Å. After vacuum depositing the following compound HT1 (400 Å), a material transferring holes, thereon, the following compound H1 (host) and the following compound D1 (dopant) in a weight ratio of 95:5 were vacuum deposited to a thickness of 300 Å as a light emitting layer. On the light emitting layer, an electron injection and transfer layer was formed to a thickness of 350 Å by vacuum depositing Compound 1 prepared in Preparation Example 1 and LiQ in a weight ratio of 7:3 to 3:7. A cathode was formed on the electron injection and transfer layer by consecutively depositing lithium fluoride (LiF) to a thickness of 12 Å and aluminum to a thickness of 2,000 Å to manufacture an organic light emitting device.

The organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-6}$ torr. The compounds used in the above-mentioned processes are as follows:

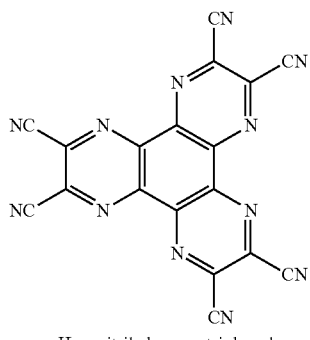
Hexanitrile hexaazatriphenylene

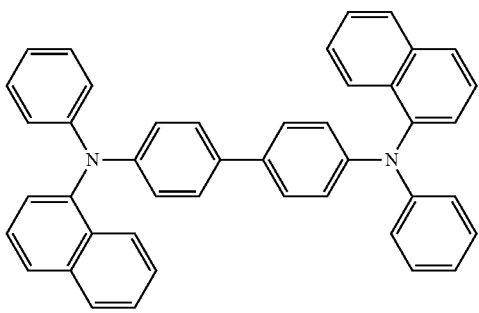
HT1

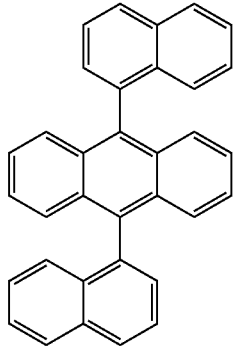
H1

-continued

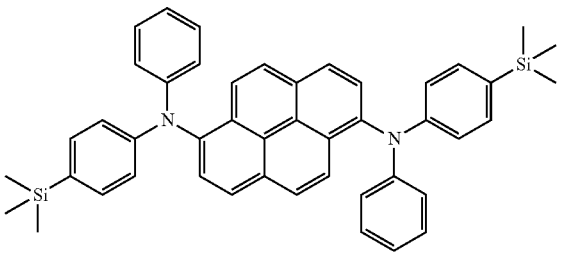
D1

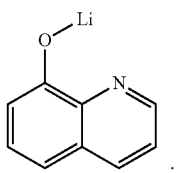
LiQ

Examples 2 to 16

Organic light emitting devices were manufactured in the same manner as in Example 1 except that compounds prepared in the preparation examples as described in the following Table 1 were each used as the compound of the electron injection and transfer layer.

Comparative Examples 1 to 6

Organic light emitting devices were manufactured in the same manner as in Example 1 except that compounds prepared in the preparation examples as described in the following Table 1 were each used as the compound of the electron injection and transfer layer. In the following Table 1, the compounds of [ET 1] to [ET 6] are as follows:

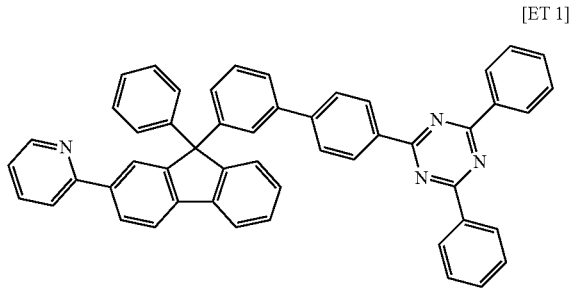
[ET 1]

[ET 2]

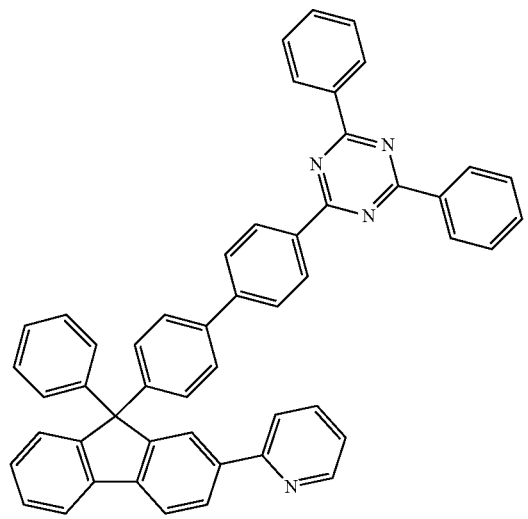

[ET 3]

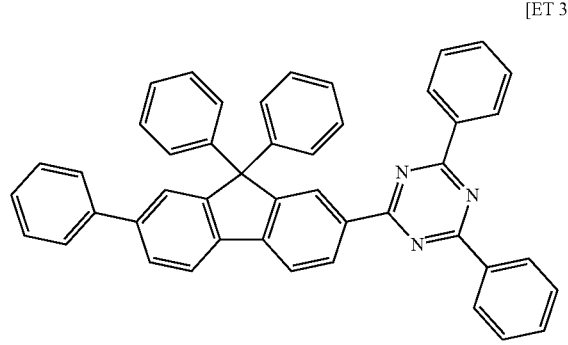

[ET 4]

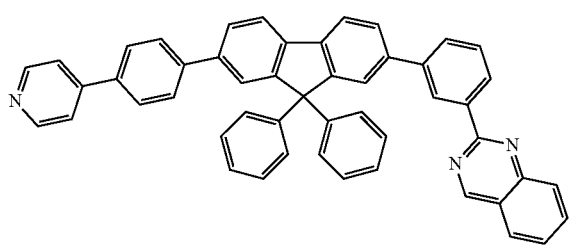

[ET 5]

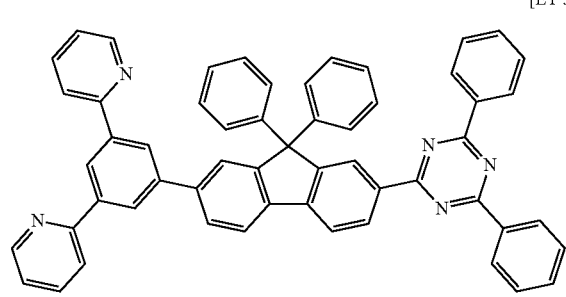

[ET 6]

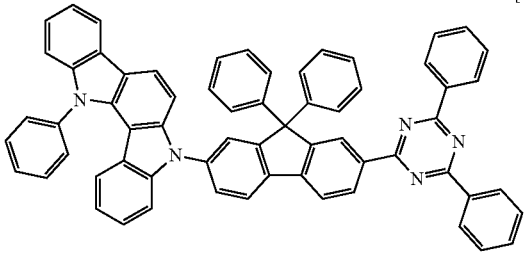

For the organic light emitting devices manufactured in the examples and the comparative examples, a driving voltage and light emission efficiency were measured at current density of 10 mA/cm2, and time taken for the luminance decreasing to 97% compared to its initial luminance (LT97) was measured at current density of 20 mA/cm2. The results are shown in the following Table 1.

TABLE 1

| | Compound | Voltage (V) | Current Efficiency (cd/A) | Color Coordinate (x, y) | Life Time (97% at 20 mA/cm$^2$) |
|---|---|---|---|---|---|
| Example 1 | Compound 2 | 3.85 | 5.21 | (0.134, 0.126) | 172 |
| Example 2 | Compound 5 | 3.81 | 5.06 | (0.134, 0.126) | 230 |
| Example 3 | Compound 6 | 3.83 | 5.27 | (0.134, 0.126) | 196 |
| Example 4 | Compound 13 | 3.80 | 5.47 | (0.134, 0.126) | 200 |
| Example 5 | Compound 15 | 3.87 | 5.33 | (0.134, 0.126) | 199 |
| Example 6 | Compound 18 | 3.88 | 5.22 | (0.134, 0.127) | 191 |
| Example 7 | Compound 28 | 3.91 | 5.06 | (0.134, 0.126) | 186 |
| Example 8 | Compound 30 | 3.84 | 5.30 | (0.134, 0.126) | 187 |
| Example 9 | Compound 31 | 3.79 | 5.22 | (0.134, 0.126) | 198 |
| Example 10 | Compound 52 | 3.75 | 5.73 | (0.134, 0.126) | 171 |
| Example 11 | Compound 61 | 3.83 | 5.19 | (0.134, 0.126) | 185 |
| Example 12 | Compound 71 | 3.88 | 5.27 | (0.134, 0.126) | 190 |
| Example 13 | Compound 78 | 3.79 | 5.67 | (0.134, 0.126) | 198 |
| Example 14 | Compound 90 | 3.74 | 5.19 | (0.134, 0.126) | 183 |
| Example 15 | Compound 105 | 3.84 | 5.26 | (0.134, 0.127) | 200 |
| Example 16 | Compound 108 | 3.88 | 5.18 | (0.134, 0.127) | 228 |
| Comparative Example 1 | [ET 1] | 4.46 | 3.89 | (0.134, 0.127) | 110 |
| Comparative Example 2 | [ET 2] | 4.57 | 3.87 | (0.135, 0.127) | 121 |
| Comparative Example 3 | [ET 3] | 4.39 | 3.88 | (0.135, 0.126) | 97 |
| Comparative Example 4 | [ET 4] | 4.65 | 3.60 | (0.134, 0.126) | 113 |
| Comparative Example 5 | [ET 5] | 4.70 | 3.75 | (0.134, 0.126) | 123 |
| Comparative Example 6 | [ET 6] | 4.68 | 3.66 | (0.134, 0.127) | 119 |

In Table 1, it was seen that the compounds of Examples 1 to 16 using the compound of Chemical Formula 1 of the present disclosure as an electron injection and control layer of the organic light emitting device exhibited properties of low driving voltage, high efficiency and long lifetime compared to the compounds of Comparative Examples 1 to 6. Particularly, as shown in Comparative Examples 1 and 2, it was identified that J-V properties became poor, a voltage rose, and efficiency and lifetime were low when a heteroaryl group and a pyridine group were attached unsymmetrically compared to when attached symmetrically on both sides of the fluorene group as in the disclosure of the present application. It was also identified that Comparative Example 3 without a pyridine group exhibited a significantly low lifetime compared to the compound having the structure of Chemical Formula 1 of the present disclosure with a pyridine group. In addition, it was identified that, when the heteroaryl group bonding to the fluorene group is a different hetero group instead of triazine or pyrimidine as in Comparative Example 4, higher driving voltage and lower efficiency were obtained compared to the compound having the structure of Chemical Formula 1 of the present disclosure. It was also identified that a material substituted with two or more pyridine groups as in Comparative Example 5 exhibited significantly higher driving voltage and lower efficiency compared to the compound having the structure of Chemical Formula 1 of the present disclosure, and lastly, it was identified that, when a bulky hetero group bonds as in Comparative Example 6, higher driving voltage and lower efficiency were obtained compared to the disclosure of the present application.

The invention claimed is:

1. A fluorene derivative of Chemical Formula 1-1 to Chemical Formula 1-3:

[Chemical Formula 1-1]

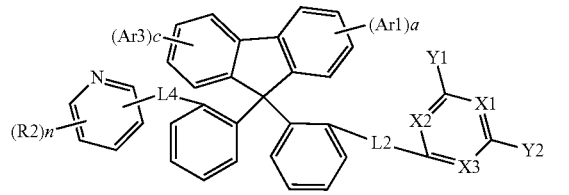

[Chemical Formula 1-2]

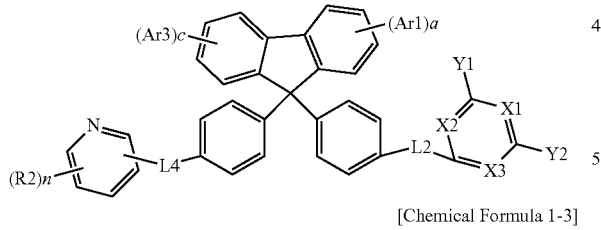

[Chemical Formula 1-3]

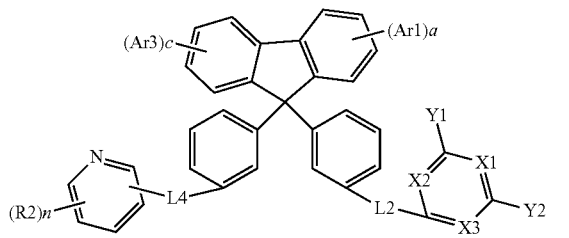

wherein, in Chemical Formula 1-1 to 1-3:

Ar1 and Ar3 are hydrogen;

L2 and L4 are the same as or different from each other, and each independently is a direct bond, a substituted or unsubstituted arylene group, or a substituted or unsubstituted heteroarylene group;

a and c are an integer of 4;

X1 to X3 are the same as or different from each other, and each independently is N or CR1;

two or more of X1 to X3 are N;

R1 and R2 are hydrogen;

Y1 and Y2 are the same as or different from each other, and each independently is deuterium, a substituted or unsubstituted alkyl group, a substituted or unsubstituted silyl group, a substituted or unsubstituted alkoxy group, a substituted or unsubstituted aryl group, or a substituted or unsubstituted heteroaryl group; and n is 4.

2. The fluorene derivative of claim 1, wherein L2 and L4 are the same as or different from each other, and each independently is a direct bond, a substituted or unsubstituted arylene group having 6 to 20 carbon atoms, or a substituted or unsubstituted monocyclic or polycyclic heteroarylene group having 3 to 20 carbon atoms.

3. The fluorene derivative of claim 1, wherein the compound of Chemical Formula 1-1 to 1-3 is any one of the following compounds:

cpd 1

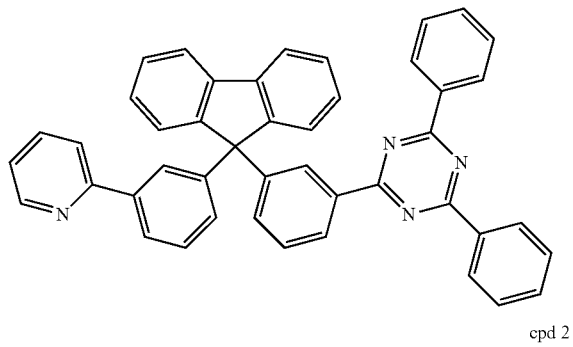

cpd 2

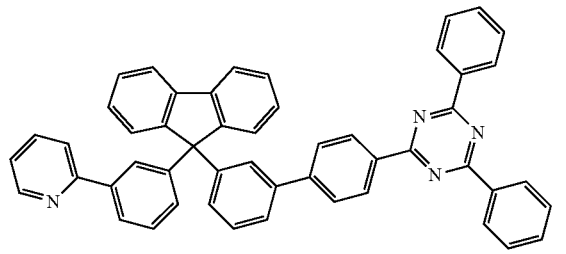

cpd 3

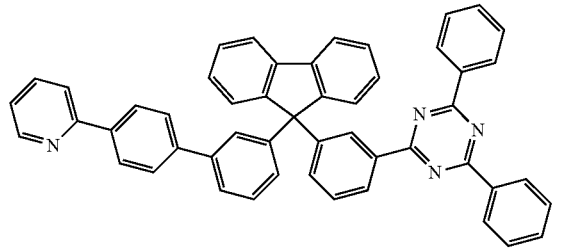

cpd 4
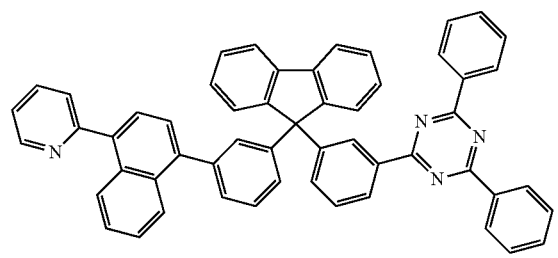
cpd 9
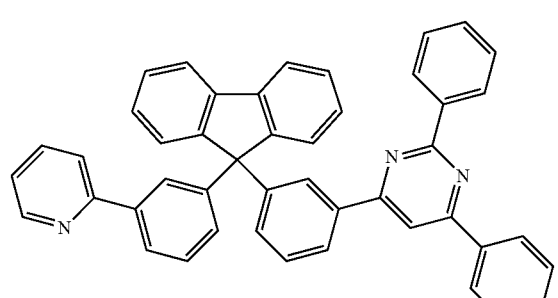
cpd 10
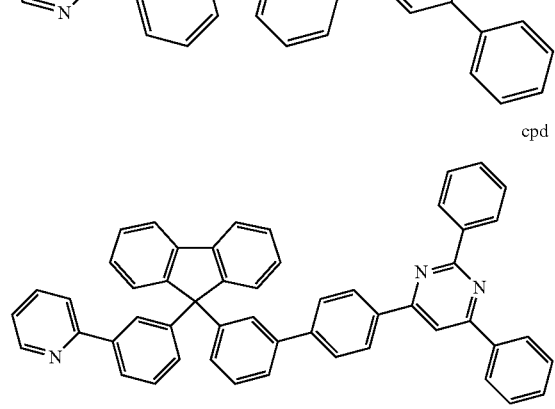
cpd 11
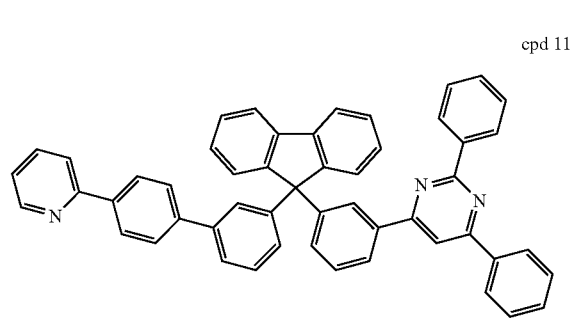
cpd 12
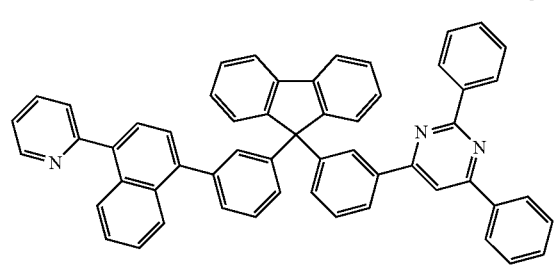
cpd 16
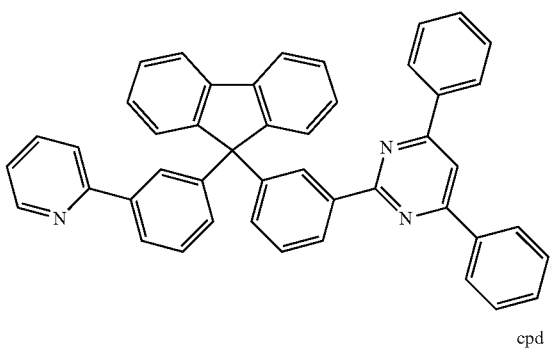
cpd 17
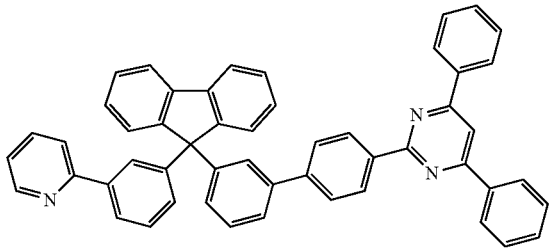
cpd 18
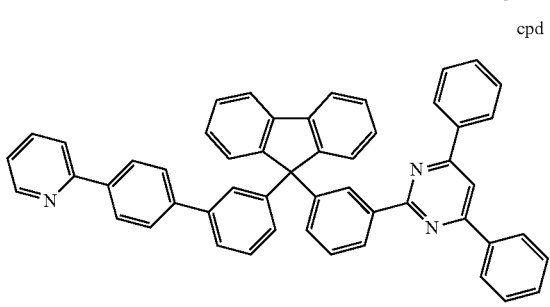
cpd 20
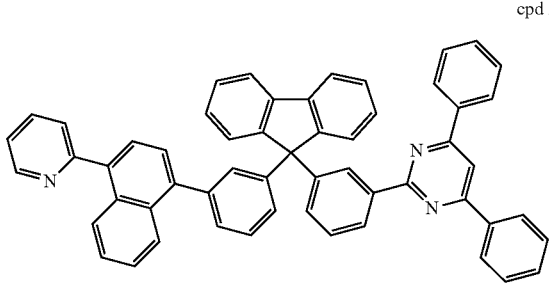
cpd 25
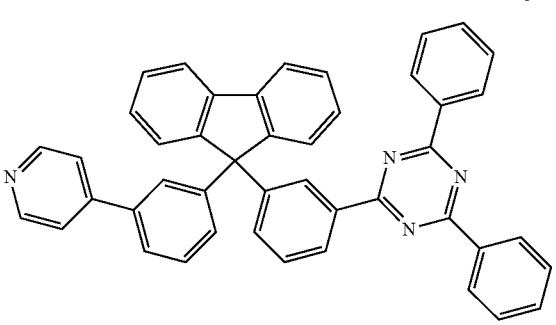

cpd 26
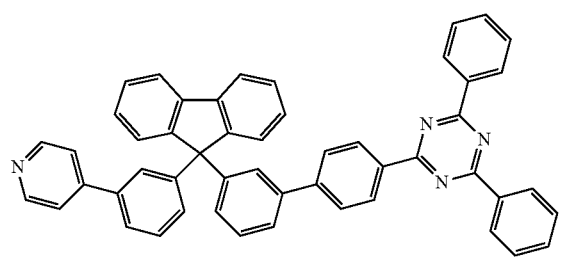
cpd 27
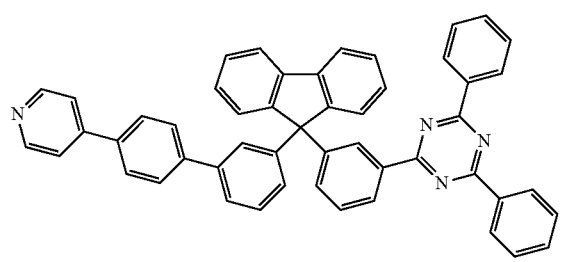
cpd 28
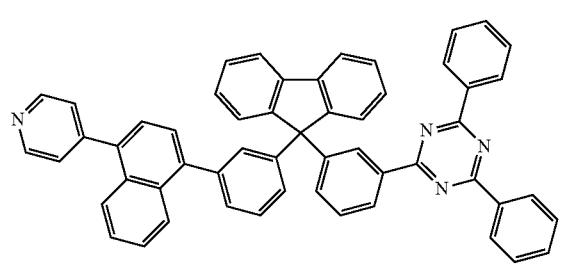
cpd 33
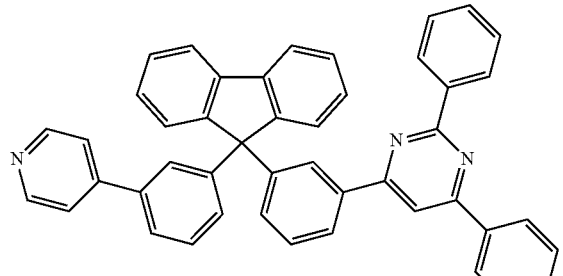
cpd 34
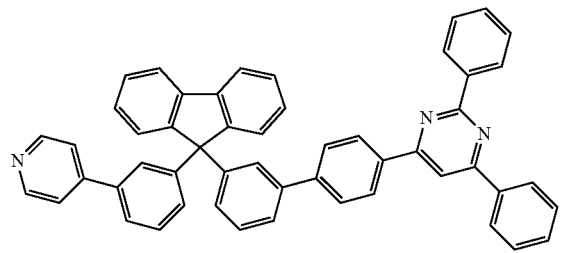
cpd 35
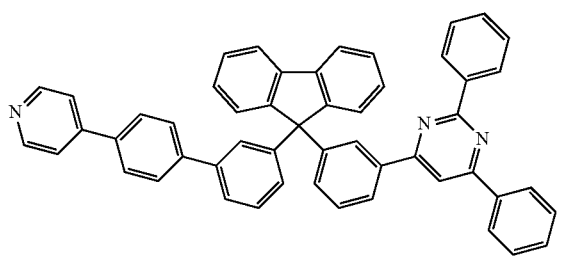
cpd 36
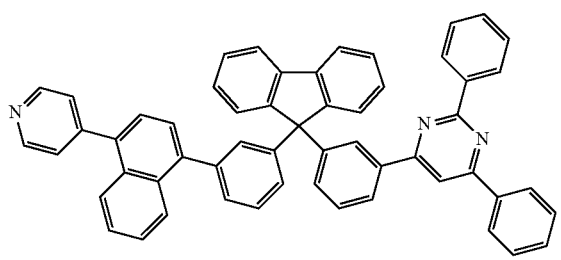
cpd 41
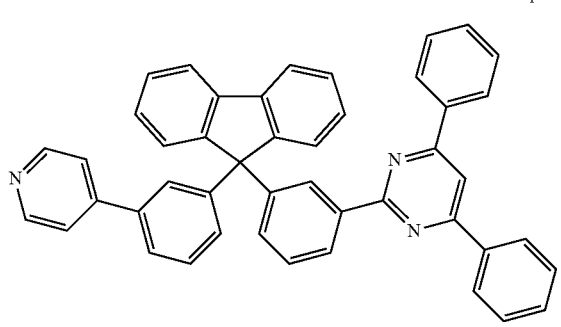
cpd 42
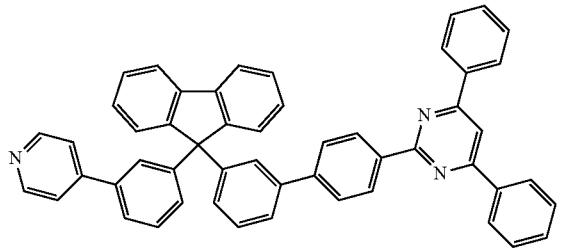
cpd 43
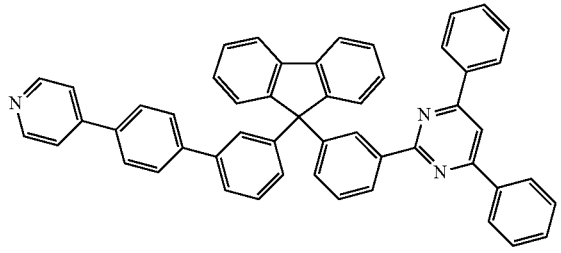

cpd 44
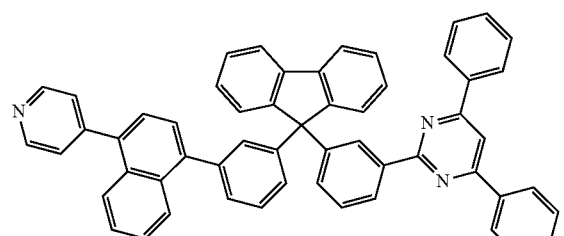
cpd 56
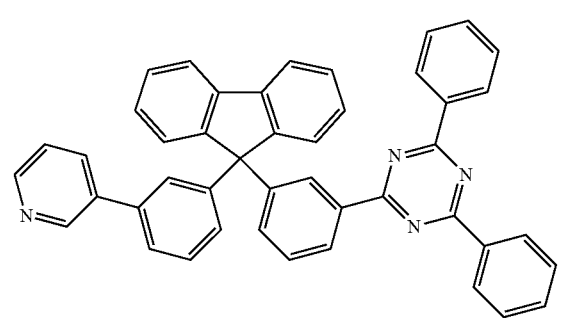
cpd 57
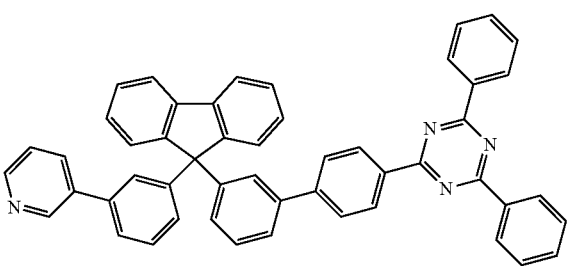
cpd 58
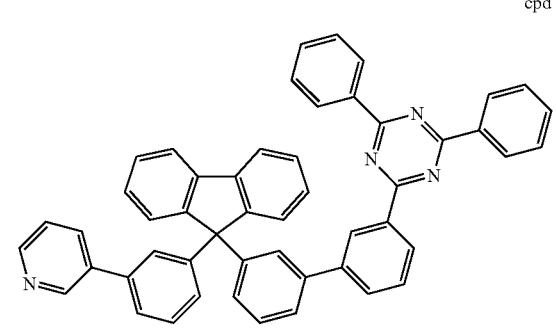
cpd 59
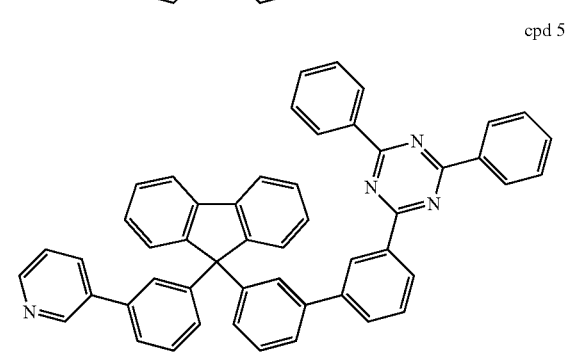
cpd 60
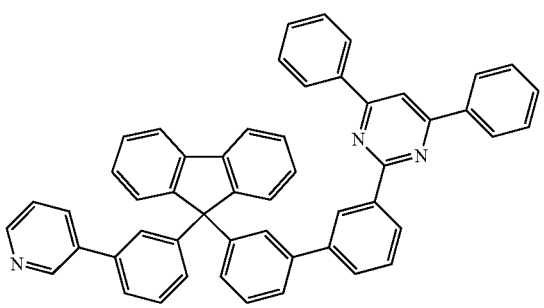
cpd 65
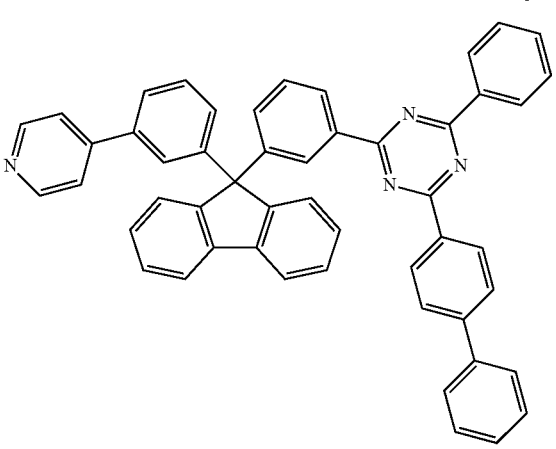
cpd 66
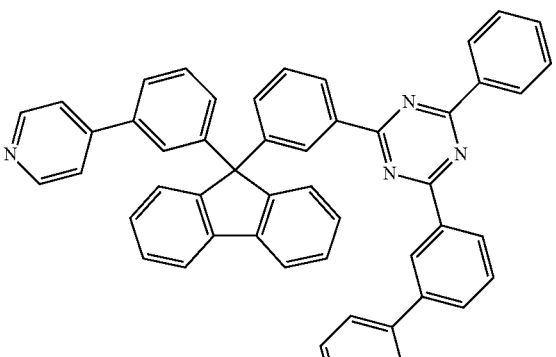
cpd 67
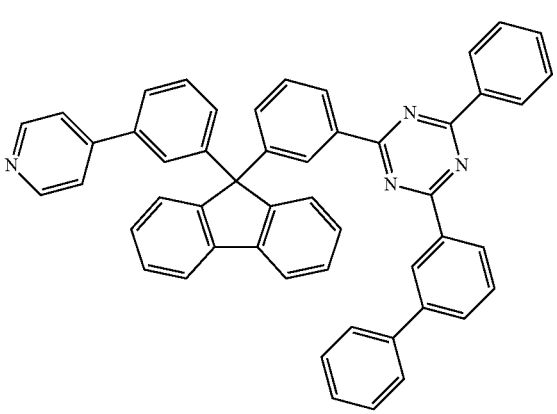

-continued
cpd 68
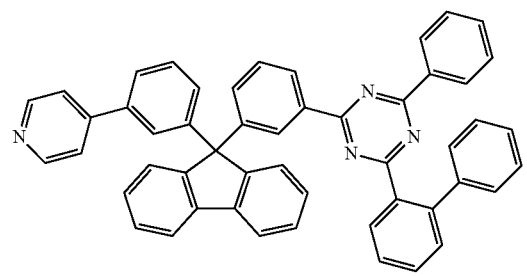
cpd 69
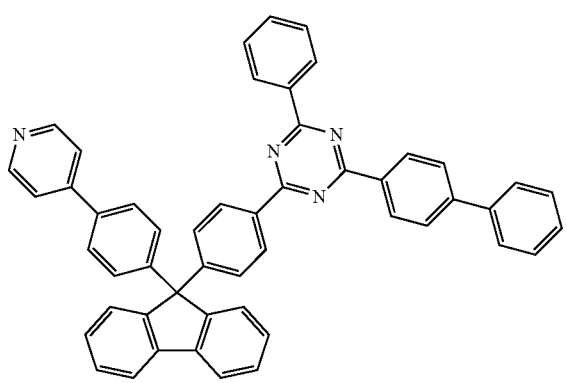
cpd 70
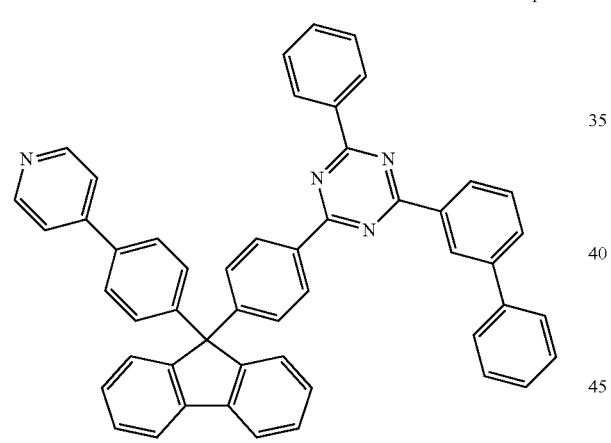
cpd 71
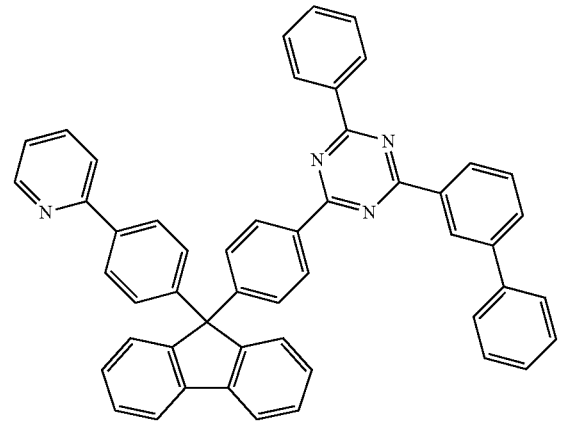
-continued
cpd 72
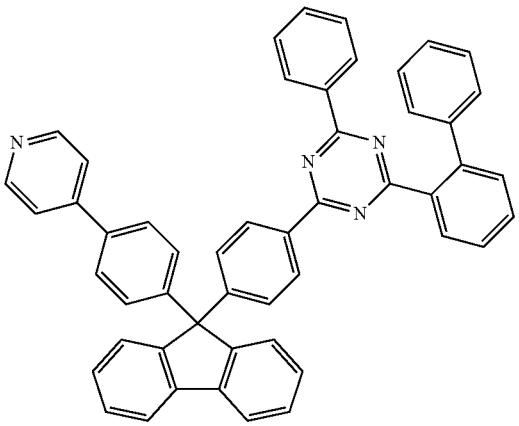
cpd 81
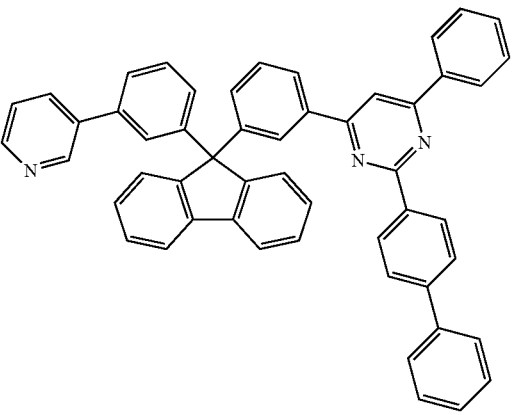
cpd 82
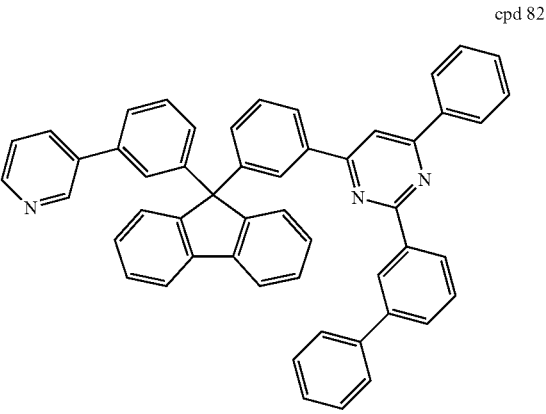

cpd 83
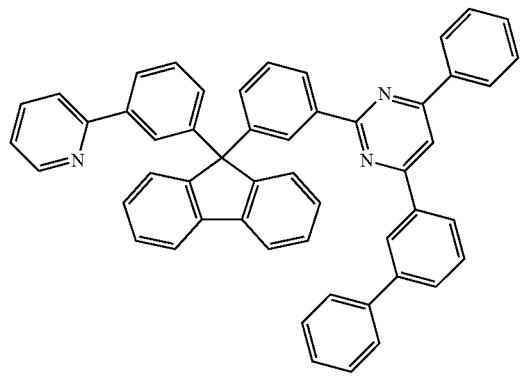
cpd 84
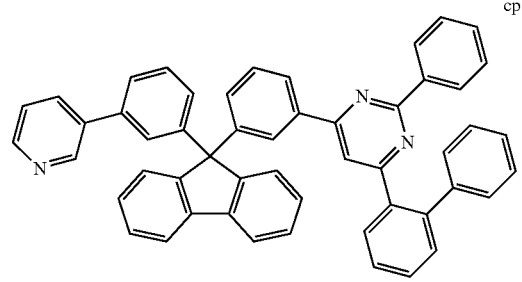
cpd 85
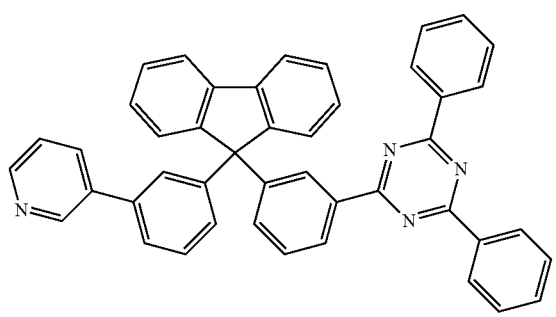
cpd 86
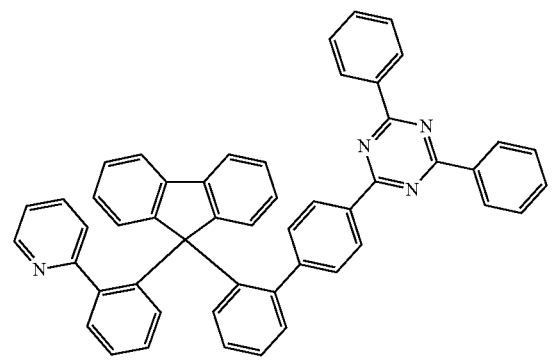
cpd 91
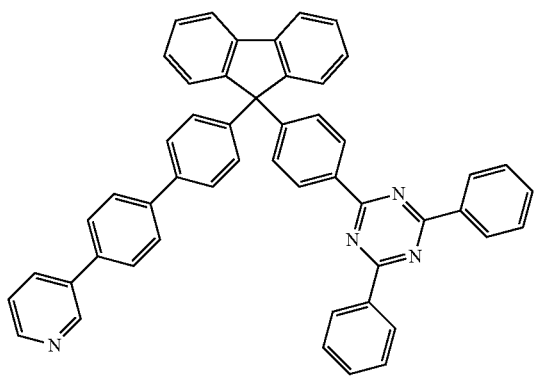
cpd 94
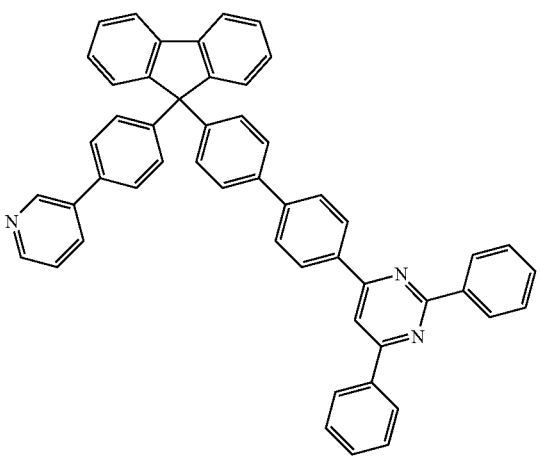
cpd 95
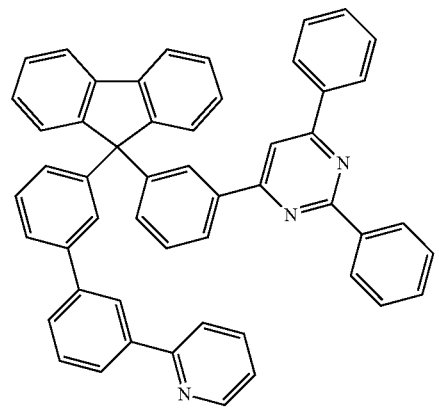
cpd 99
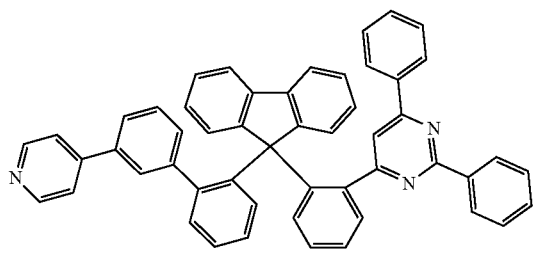

cpd 101

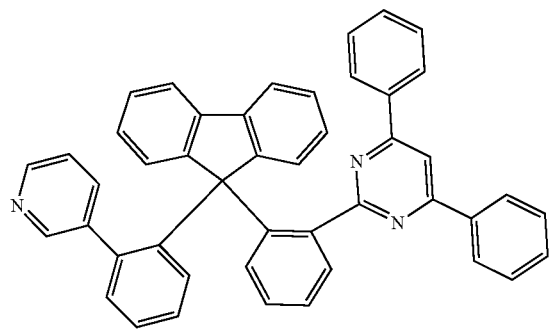

cpd 102

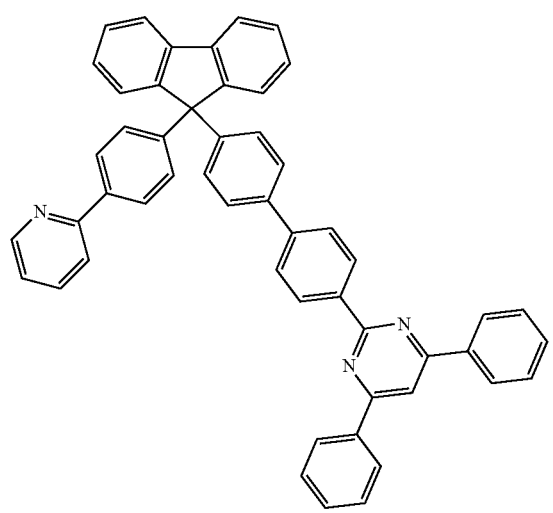

cpd 104

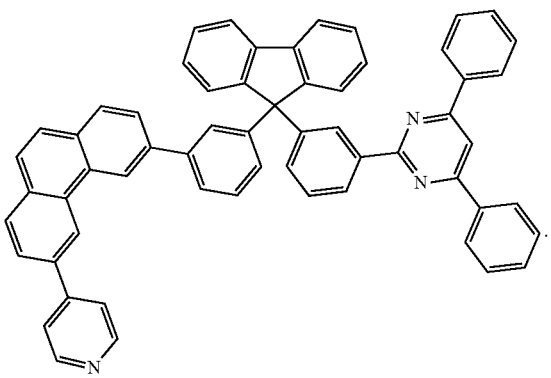

4. An organic light emitting device comprising:
a first electrode;
a second electrode provided opposite to the first electrode; and
one, two or more organic material layers provided between the first electrode and the second electrode,
wherein one or more layers of the one, two or more organic material layers includes the fluorene derivative of claim 1.

5. The organic light emitting device of claim 4, wherein the one, two or more organic material layers includes a light emitting layer, and the light emitting layer includes the fluorene derivative.

6. The organic light emitting device of claim 4, wherein the one, two or more organic material layers includes a hole injection layer or a hole transfer layer, and the hole injection layer or the hole transfer layer includes the fluorene derivative.

7. The organic light emitting device of claim 4, wherein the one, two or more organic material layers includes an electron injection layer, an electron transfer layer, or an electron injection and transfer layer, and the electron injection layer, the electron transfer layer, or the electron injection and transfer layer includes the fluorene derivative.

8. The organic light emitting device of claim 4, wherein the one, two or more organic material layers includes an electron control layer, and the electron control layer includes the fluorene derivative.

* * * * *